(12) United States Patent
Shiina et al.

(10) Patent No.: US 9,315,442 B2
(45) Date of Patent: Apr. 19, 2016

(54) METHOD FOR MANUFACTURING OPTICALLY ACTIVE CARBOXYLIC ACID ESTER

(75) Inventors: Isamu Shiina, Tokyo (JP); Kenya Nakata, Tokyo (JP); Keisuke Ono, Tokyo (JP)

(73) Assignee: TOKYO UNIVERSITY OF SCIENCE EDUCATIONAL FOUNDATION ADMINISTRATIVE ORGANIZATION, Tokyo (JP)

( * ) Notice: Subject to any disclaimer, the term of this patent is extended or adjusted under 35 U.S.C. 154(b) by 4 days.

(21) Appl. No.: 14/124,068

(22) PCT Filed: Jun. 7, 2012

(86) PCT No.: PCT/JP2012/064647
§ 371 (c)(1),
(2), (4) Date: Dec. 5, 2013

(87) PCT Pub. No.: WO2012/169575
PCT Pub. Date: Dec. 13, 2012

(65) Prior Publication Data
US 2014/0135520 A1    May 15, 2014

(30) Foreign Application Priority Data
Jun. 10, 2011   (JP) .................................. 2011-130572

(51) Int. Cl.
| | |
|---|---|
| *C07C 69/76* | (2006.01) |
| *C07C 67/08* | (2006.01) |
| *C07D 317/68* | (2006.01) |
| *C07B 57/00* | (2006.01) |
| *C07D 207/337* | (2006.01) |
| *C07D 209/26* | (2006.01) |
| *C07D 209/46* | (2006.01) |
| *C07D 209/88* | (2006.01) |
| *B01J 31/02* | (2006.01) |

(52) U.S. Cl.
CPC ............. *C07C 67/08* (2013.01); *B01J 31/0241* (2013.01); *C07B 57/00* (2013.01); *C07D 207/337* (2013.01); *C07D 209/26* (2013.01); *C07D 209/46* (2013.01); *C07D 209/88* (2013.01); *C07D 317/68* (2013.01); *B01J 2231/49* (2013.01); *C07B 2200/07* (2013.01); *C07C 2101/08* (2013.01); *C07C 2103/26* (2013.01)

(58) Field of Classification Search
CPC ...................................................... C07C 59/48
USPC ........................................................ 560/105
See application file for complete search history.

(56) References Cited

U.S. PATENT DOCUMENTS

2010/0234610 A1    9/2010 Shiina et al.

FOREIGN PATENT DOCUMENTS

WO    WO 2008/140074    11/2008
WO    WO 2009/113428    9/2009

OTHER PUBLICATIONS

Ono et al., The Chemical Society of Japan 2011.*
Isamu Shiina, Kenya Nakata, Keisuke Ono, Yu-Suke Onda and Makoto Itagaki: "Kinetic Resolution of Racemic alpha-Arylalkanoic Acid with Achiral Alcohols via the Asymmetric Esterification Using Carboxylic Anhydrides and Acyl-Transfer Catalysts", Journal of the American Chemical Society, vol. 132, Aug. 3, 2010, pp. 11629-11641, XP002732442, DOI: 10.1021/ja103490h.
Ono Keisuke et al.: "Fusei Ester-ka Hannoo Mochiita Racemic Carboxylic Acid no Sokudoronteki Kogaku Bunkatsu ni Okeru Yobai Koka = Solvent Effects on the Catalytic Asymmetric Esterification Using MA-BTM COmbined System in the Kinetic Resolution of Racemic Carboxylic Acids", 91st Annual Meeting of the Chemical Society of Japan in Spring (2011) Koen Yokoshu IV,, Mar. 11, 2011, p. 1228, XP008172952.
Isamu Shiina, Kenya Nakata and Yu-Suke Onda: "Kinetic Resolution of Racemic Carboxylic Acids Using Achiral Alcohols by the Promotion of Benzoic Anhydrides and Tetramisole Derivatives: Production of Chiral Nonsteroidal Anti-Inflammatory Drugs and Their Esters", European Journal of Organic Chemistry, Nov. 4, 2008, pp. 5887-5890, XP002732443, DOI: 10.1002/ejoc.200800942.
Extended European Search Report in EP Application No. 12796965.7, mailed Dec. 9, 2014.
Birman et al., "Benzotetramisole: A Remarkably Enantioselective Acyl Transfer Catalyst," Organic Letters, vol. 8, No. 7, pp. 1351-1354, 2006.
Birman et al., "Kinetic Resolution of Propargylic Alcohols Catalyzed by Benzotetramisole," Organic Letters, vol. 8, No. 21, pp. 4859-4861, 2006.
Ebbers et al., "Controlled Racemization of Optically Active Organic Compounds: Prospects for Asymmetric Transformation," Tetrahedron Report No. 43, Tetrahedron, vol. 53, No. 28, pp. 9417-9476, 1997.
Ono et al., "Solvent Effects on the Catalytic Asymmetric Esterification Using MA-BTM Combined System in the Kinetic Resolution of Racemic Carboxylic Acids," The Chemical Society of Japan, 2011.

* cited by examiner

*Primary Examiner* — Yong Chu
*Assistant Examiner* — Sonya Wright
(74) *Attorney, Agent, or Firm* — Knobbe Martens Olson & Bear LLP

(57) ABSTRACT

A method that manufacturers an optically active carboxylic acid ester at high yield and high enantioselectivity is provided. An optically active carboxylic acid ester is manufactured at high yield and high enantioselectivity by reacting a racemic carboxylic acid and a specific alcohol or phenol derivatives in a polar solvent having a dipole moment of 3.0 or higher in the presence of an acid anhydride and an asymmetric catalyst, esterifying one enantiomer of the racemic carboxylic acid at high selectivity, and increasing the amount of esterified carboxylic acid by racemizing the optically active carboxylic acid which is the other enantiomer not used in esterification.

19 Claims, No Drawings

METHOD FOR MANUFACTURING OPTICALLY ACTIVE CARBOXYLIC ACID ESTER

This application is the U.S. National Phase under 35 U.S.C. §371 of International Application PCT/JP2012/064647, filed Jun. 7, 2012, designating the U.S., and published in Japanese as WO 2012/169575 on Dec. 13, 2012, which claims priority to Japanese Patent Application No. 2011-130572, filed Jun. 10, 2011, the entire contents of which are incorporated herein by reference.

TECHNICAL FIELD

The present invention relates to a method for manufacturing an optically active carboxylic acid ester according to dynamic kinetic resolution, and in more detail, relates to a method for manufacturing an optically active carboxylic acid ester in high yield by selectively esterifying one enantiomer of a racemic carboxylic acid, as well as racemizing an optically active carboxylic acid that is the other enantiomer to increase the amount of the required enantiomer.

BACKGROUND ART

Optically active carboxylic acid esters are used in various fields such as pharmaceutical products, intermediates of biologically active substances, intermediates of natural product synthesis, and the like.

Conventionally, as a method for manufacturing optically active carboxylic acid esters, a method has been known by way of reaction between an alcohol and carboxylic acid using an asymmetric catalyst.

As a method for manufacturing an optically active carboxylic acid ester as well as an optically active alcohol, a method has been known that uses tetramisole or benzotetramisole as a catalyst, and produces the optically active carboxylic acid ester from a racemic secondary benzyl alcohol in the presence of an acid anhydride (see Non-Patent Document 1). In addition, a method for manufacturing an optically active carboxylic acid ester from a racemic propargylic alcohol in the presence of an acid anhydride using benzotetramisole as a catalyst has been known (see Non-Patent Document 2). Furthermore, a method for manufacturing an optically active carboxylic acid ester by reacting a racemic secondary alcohol and a carboxylic acid in the presence of a benzoic anhydride or a derivative thereof, using tetramisole or benzotetramisole as a catalyst has also been known as a method improving substrate universality (see Patent Document 1).

On the other hand, a method for manufacturing an optically active carboxylic acid ester by reacting a racemic carboxylic acid and an alcohol in the presence of a benzoic anhydride or a derivative thereof, using tetramisole or benzotetramisole as a catalyst has also been known as a method for manufacturing an optically active carboxylic acid ester along with an optically active carboxylic acid (see Patent Document 2).

Patent Document 1: PCT International Publication No. WO2008/140074
Patent Document 2: PCT International Publication No. WO2009/113428
Non-Patent Document 1: Birman, V. B.; Li, X.; Org. Lett.; 2006, 8, (7), p. 1351-1354
Non-Patent Document 2: Birman, V. B.; Guo, L.; Org. Lett.; 2006, 8, (21), p. 4859-4861
Non-Patent Document 3: Ebbers, E. J. et al.; Tetrahedron; 1997, 53, (28), p. 9417-9476

DISCLOSURE OF THE INVENTION

Problems to be Solved by the Invention

These methods can only produce an optically active carboxylic acid ester at 50% yield theoretically, since one of the racemic alcohol or racemic carboxylic acid of the source materials is selectively esterified. If the other enantiomer that was not be esterified could be racemized, it is considered possible to produce only the required optically active carboxylic acid ester; however, such a method has not been proposed until now.

In this regard, a method of heating to high temperature along with a base has been known as a method for racemizing an optically active carboxylic acid (see Non-Patent Document 3). However, for severe heating conditions, there have been constraints such as corrosion resistant equipment becoming necessary, and requiring separating unreacted carboxylic acid from the optically active carboxylic acid ester and then performing racemization. For this reason, a method has been desired that can realize racemization of optically active carboxylic acid at mild conditions, and obtain the sought optically active carboxylic acid ester at high yield.

The present invention, in consideration of the above problems, has the objective of providing a method for manufacturing an optically active carboxylic acid ester in high yield by selectively esterifying one enantiomer of a racemic carboxylic acid, as well as racemizing an optically active carboxylic acid that is the other enantiomer to increase to proportion of the required enantiomer.

Means for Solving the Problems

The present inventors carried out diligent research to solve the above problem. As a result, they achieved the completion of the present invention by discovering that the above problem can be solved by reacting a racemic carboxylic acid and a specified alcohol or phenol derivative under specified conditions. More specifically, the present invention is as follows.

A first aspect of the present invention is a method for manufacturing an optically active carboxylic acid ester according to dynamic kinetic resolution, the method including: reacting a racemic carboxylic acid and an alcohol represented by formula (a) below or a phenol derivative represented by formula (b) below under the presence of an acid anhydride and an asymmetric catalyst in a polar solvent with a dipole moment of 3.0 or higher, thereby selectively esterifying one enantiomer of the racemic carboxylic acid, while racemizing the other enantiomer, in which formula (a) has the structure

in the formula (a), $R^a$ represents a phenyl group, naphthyl group, anthryl group, or phenanthryl group, which may have a substituent group, and formula (b) has the structure

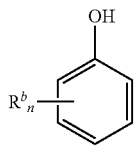

(b)

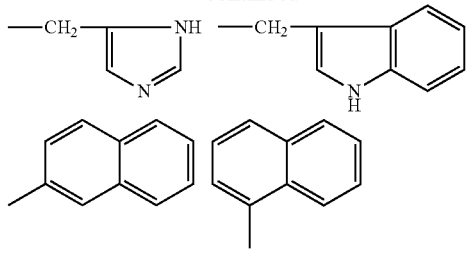

in the formula (b), $R^b$ represents a phenyl group, naphthyl group, anthryl group, or phenanthryl group, which may have a substituent group, n represents an integer of 1 to 5, and in the case that a plurality of $R^b$ is present, they may be the same or different.

According to a second aspect of the present invention, in the method for manufacturing an optically active carboxylic acid ester as described in the first aspect, the asymmetric catalyst is represented by formulas (c) to (f) below:

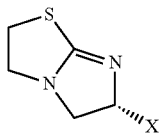

(c)

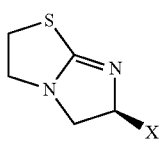

(d)

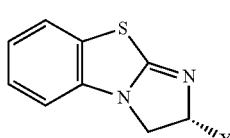

(e)

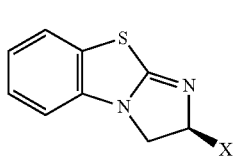

(f)

in the formulas (c) to (f), X represents any of the following substituent groups,

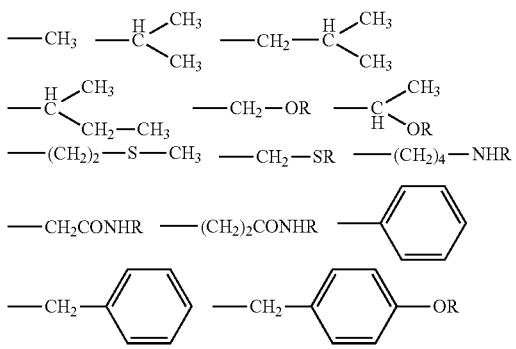

and R represents a protecting group.

According to a third aspect of the present invention, in the method for manufacturing an optically active carboxylic acid ester as described in the first or second aspect, the racemic carboxylic acid is represented by formula (g) below:

(g)

$$\underset{R^{g1}}{\overset{R^{g2}}{\underset{\text{HO}}{\overset{\text{O}}{\bigvee}}}}$$

in the formula (g), $R^{g1}$ and $R^{g2}$ represent organic groups which differ from each other.

According to a fourth aspect of the present invention, in the method for manufacturing an optically active carboxylic acid ester as described in the third aspect, either one of $R^{g1}$ and $R^{g2}$ in the formula (g) is an organic group binding with an asymmetric carbon via a carbon atom having a multiple bond, and the other one is an organic group binding with an asymmetric carbon via a carbon atom not having a multiple bond.

Effects of the Invention

According to the present invention, it is possible to produce an optically active carboxylic acid ester in high yield by selectively esterifying one enantiomer of a racemic carboxylic acid, as well as racemizing an optically active carboxylic acid that is the other enantiomer to increase the amount of esterified carboxylic acid.

PREFERRED MODE FOR CARRYING OUT THE INVENTION

A method for manufacturing an optically active carboxylic acid ester according to the present invention is characterized by reacting a racemic carboxylic acid and a specific alcohol or phenol derivative under the presence of an acid anhydride and asymmetric catalyst, in a polar solvent with a dipole moment of 3.0 or higher, thereby selectively esterifying one enantiomer of the racemic carboxylic acid, while racemizing the other enantiomer.

(Racemic Carboxylic Acid)

The racemic carboxylic acid used in the manufacturing method of the present invention is not particularly limited; however, one having an asymmetric carbon at the α-position of the carboxyl group as in the following formula (g) is preferable.

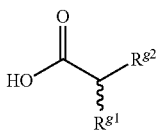
(g)

In the above formula (g), $R^{g1}$ and $R^{g2}$ represent organic groups that are different from each other. As the organic groups, an alkyl group, alkenyl group, alkynyl group, aryl group, heteroaryl group, alkoxyalkyl group, alkoxyalkenyl group, alkoxyalkynyl group, arylalkyl group, arylalkenyl group, arylalkynyl group, heteroarylalkyl group, heteroarylalkenyl group, heteroarylalkynyl group, alkylaryl group, alkylheteroaryl group, alkoxyaryl group, alkoxyheteroaryl group, etc. can be exemplified. This organic group may be arbitrarily substituted by an alkyl group, alkoxy group, aryl group, heteroaryl group, acyl group, halogen atom, etc.

In addition, it is preferable for either one of $R^{g1}$ and $R^{g2}$ to be an organic group binding with an asymmetric carbon via a carbon atom having a multiple bond, and the other one to be an organic group binding with an asymmetric carbon via a carbon atom not having a multiple bond. The enantiomeric excess ratio can thereby be raised. As the organic group that can bind with an asymmetric carbon via a carbon atom having a multiple bond, an aryl group is preferable, and as the organic that can bind with an asymmetric carbon via a carbon atom not having a multiple bond, an alkyl group is preferable. These aryl groups and alkyl groups may have substituent group(s).

(Alcohol)

The alcohol used in the manufacturing method of the present invention is represented by the following formula (a).

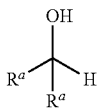
(a)

In the above formula (a), $R^a$ represents a phenyl group, naphthyl group, anthryl group or phenanthryl group that may have a substituent group. As the substituent group of $R^a$, an alkyl group, alkoxy group, aryl group, halogen atom, etc. can be exemplified. In particular, a 2-tolyl group, 1-naphthyl group and 9-phenanthryl group are preferable as $R^a$. By using such an alcohol, it is possible to manufacture an optically active carboxylic acid ester with high enantiomeric excess ratio.

(Phenol Derivative)

The phenol derivative used in the manufacturing method of the present invention is represented by the following formula (b).

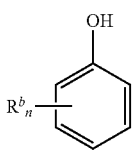
(b)

In the above formula (b), $R^b$ represents a phenyl group, naphthyl group, anthryl group or phenanthryl group that may have a substituent group, and a naphthyl group is preferable. As the substituent group of $R^b$, an alkyl group, alkoxy group, aryl group, halogen atom, etc. can be exemplified. n is an integer of 1 to 5, and n=2 is preferable. In the case of multiple $R^b$ being present, these may be the same or may be different. Among such phenol derivatives, one in which the 2- and 6-positions of phenol are substituted by naphthyl groups is preferable.

(Acid Anhydride)

The acid anhydride used in the manufacturing method of the present invention functions as a dehydrating condensing agent. As the acid anhydride, one obtained from benzoic acid, benzoic acid where an electron-donating group such as an alkyl group, alkoxy group, amino group or alkoxyalkyl group is bonded to the phenyl group, or from a multisubstituted carboxylic acid in which the α-position is a quaternary carbon is preferable, and one obtained from benzoic acid, a 1 to 3 substituted benzoic acid group with alkyl groups or alkoxy groups of 1 to 3 carbons bonded thereto, pivalic acid, 2-methyl-2-phenylpropionic acid, or 2,2-diphenylpropionic acid is more preferable.

(Asymmetric Catalyst)

The asymmetric catalyst used in the manufacturing method of the present invention is not particularly limited; however, one represented by the following formulas (c) to (f) is preferable.

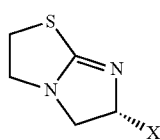
(c)

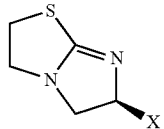
(d)

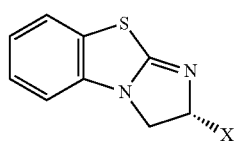
(e)

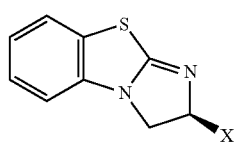
(f)

In the above formulas (c) to (f), X represents any of the following substituent groups. R is a protecting group such as an alkyl group, acyl group and silyl group.

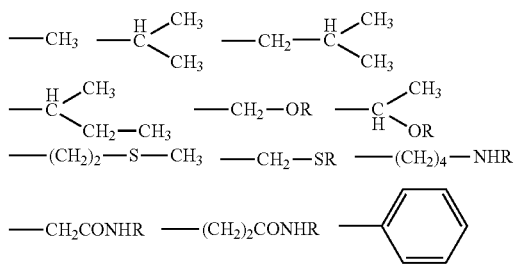

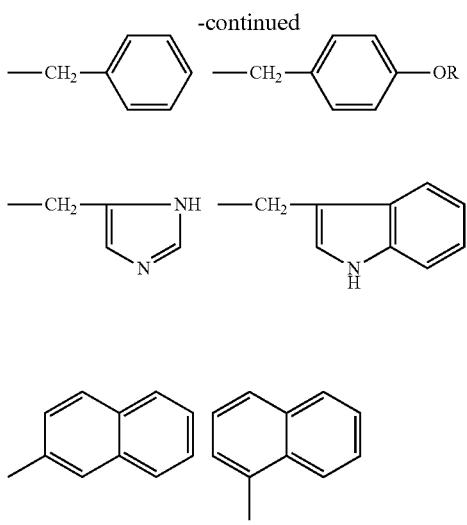

Among the asymmetric catalysts represented by the above formulas (c) to (f), catalysts represented by the above formula (c) or (d) and in which X is a phenyl group are called tetramisoles, and catalysts represented by the above formula (e) or (f) and in which X is a phenyl group are called benzotetramisoles. These catalysts can be obtained as commercial goods, and can be synthesized using an amino acid having a substituent group represented by X as a side chain.

(Polar Solvent)

The polar solvent used in the manufacturing method of the present invention has a dipole moment of 3.0 or higher. As such a polar solvent, acetonitrile, N-methylpyrrolidone, N,N-dimethylformamide, N,N-dimethylacetamide, 1,3-dimethyl-2-imidazolidinone, dimethylsulfoxide, etc. can be exemplified. By using a polar solvent having a dipole moment of 3.0 or higher, racemization of the optically active carboxylic acid occurs more easily.

(Reaction Conditions, Etc.)

Manufacture of the optically active carboxylic acid ester is performed by adding the racemic carboxylic acid, alcohol or phenol derivative, acid anhydride and asymmetric catalyst into the polar solvent; however, a base is preferably added into the reaction system. As this base, an organic base that does not have nucleophilicity is preferable, and trimethylamine, triethylamine, diisopropylethylamine, etc. can be exemplified. Although the addition sequence to the polar solvent is arbitrary, it is preferable to sequentially add the alcohol or phenol derivative, organic base and asymmetric catalyst into a solution containing the racemic carboxylic acid and acid anhydride.

The added amounts of each are not particularly limited; however, the alcohol or phenol derivative is preferably used in at least an equivalent amount to the racemic carboxylic acid in order for the racemic carboxylic acid to be completely consumed and convert to the optically active carboxylic acid ester, and is more preferably used in 1.0 to 1.5 equivalents. The acid anhydride is necessary in order to make a mixed acid anhydride with the racemic carboxylic acid and form an intermediate that causes enantioselective esterification to progress, and is preferably used in at least an equivalent amount to the racemic carboxylic acid, and more preferably used in 1.0 to 5 equivalents. The base has an action of neutralizing the acid derived from the acid anhydride generated accompanying reaction progression, and an action of promoting racemization of the mixed acid anhydride activated by the asymmetric catalyst. Although the reaction will progress even without adding a base, in order to promote racemization and raise the yield of the targeted carboxylic acid ester and enantioselectivity, it is preferable to add 1.2 to 4.8 equivalents relative to the racemic carboxylic acid. The asymmetric catalyst is necessary in order to cause esterification to progress enantioselectively, and is preferably used in 0.1 to 10 mol % relative to the racemic carboxylic acid. The reaction temperature is preferably −23 to 30° C., and the reaction time is preferably 10 minutes to 72 hours.

An example of the reaction mechanism in the method for manufacturing optically active carboxylic acid ester according to dynamic kinetic resolution is shown below. The following reaction mechanism is an example in the case of respectively using 2-phenylpropionic acid as the racemic carboxylic acid, di(1-naphthyl)methanol as the alcohol, pivalic acid anhydride as the acid anhydride, and (+)-benzotetramisole as the asymmetric catalyst.

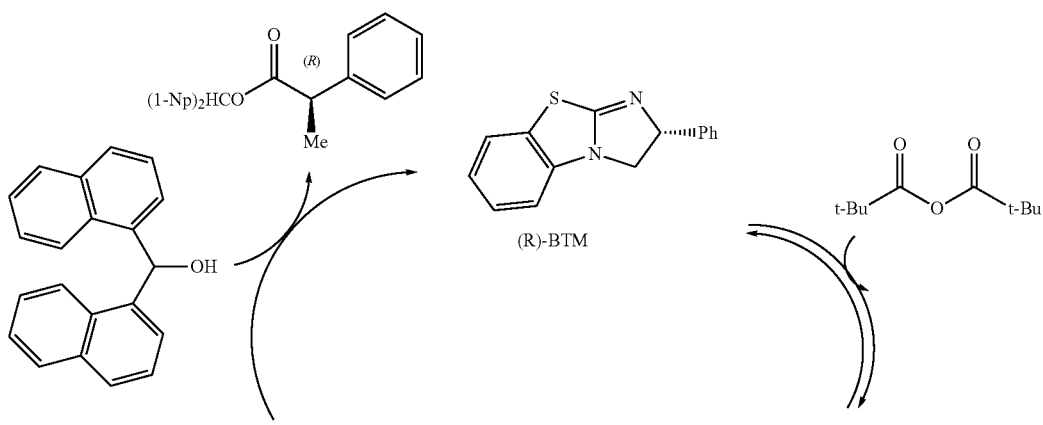

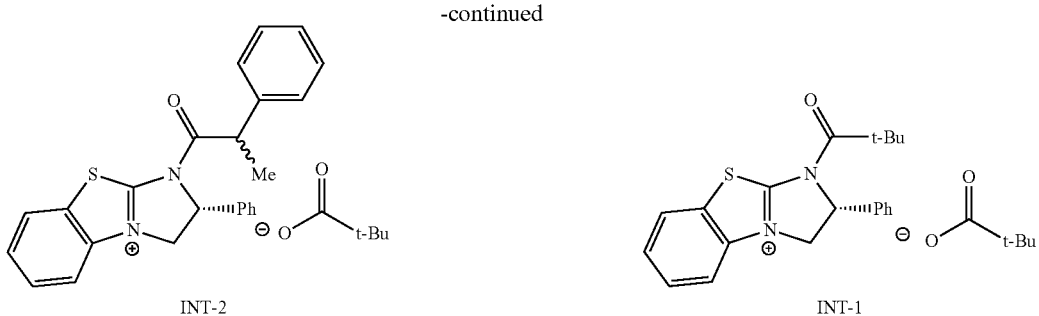

In the present reaction, first, an amphoteric intermediate INT-1 is formed from the asymmetrical catalyst (+)-benzotetramisole ((R)-BTM) and the acid anhydride, the carboxylic acid reacts with this, and a mixed acid anhydride (+/−)-MA consisting of the carboxylic acid and the acid anhydride is formed. (R)-MA and (S)-MA are activated by the asymmetric catalyst, and amphoteric intermediates INT-2 corresponding to each are formed; however, only the intermediate derived from (R)-MA selectively reacts with the alcohol, which is a nucleophile, and (R)-carboxylic acid ester is produced. On the other hand, the remaining half of (S)-MA forms (S)-carboxylic acid when hydrolyzed, and if hydrolysis is not carried out, since (R)-MA and (S)-MA are in an equilibrium state in the polar solvent, racemization is promoted herein. If an organic base such as an amine is present, the rate of this equilibrium reaction is accelerated, and thus racemization is promoted.

EXAMPLES

Although Examples of the present invention will be explained hereinafter, the scope of the present invention is not to be limited to these Examples.

In the below Examples, the following asymmetric catalyst was used.

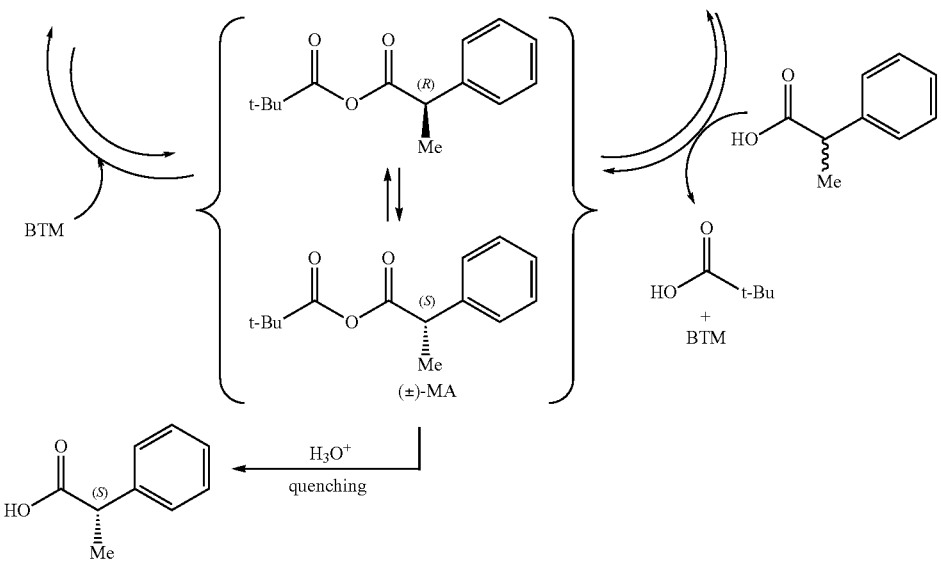

(R)-BTM

Experimental Example 1

Effects of Reaction Solvent (1)

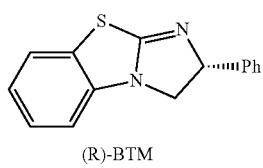 [SMILES: c1ccc([C@@H]2CN3C(=N2)Sc2ccccc23)cc1]

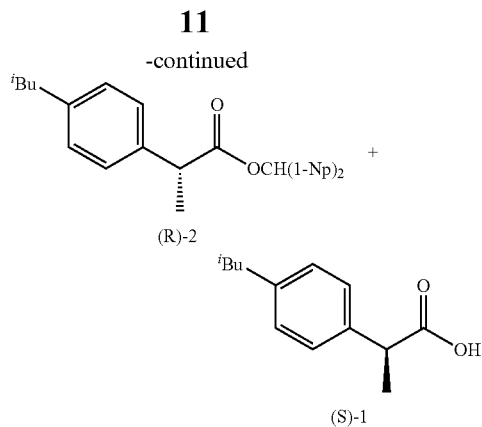

(R)-2

(S)-1

As shown in the above reaction equation, the effects of the solvent have been considered in dynamic kinetic resolution by asymmetric esterification with di(1-naphthyl)methanol (3) with ibuprofen (1) as a substrate.

To 1 equivalent of ibuprofen (1) in 0.2 moles of each solvent shown in Table 1, 1.2 equivalents of pivalic acid anhydride, 0.5 equivalents of di(1-naphthyl)methanol (3), 1.8 equivalents of diisopropylethylamine and 5 mol % (+)-benzotetramisole were added, and were allowed to react for 12 hours at room temperature in accordance with the chemical equation. After cooling the reaction system to 0° C., 1N hydrochloric acid was added to stop the reaction. After isolating the organic layer, the aqueous layer was extracted with ethyl acetate. After combining the organic layer and drying with anhydrous sodium sulfate, a crude product was obtained by filtering and vacuum concentrating. The generated optically active ester and unreacted optically active carboxylic acid were separated by way of silica gel thin layer chromatography to obtain the respective compounds.

The enantiomeric excess ratio (ee) was determined by HPLC analysis with a chiral column.

The s value was calculated as follows by way of the method of Kagan (Top. Stereochem., 1988, Vol. 18, pp. 249-330).

$$s=[\ln(1-C)(1-ee \text{ of recovery alcohol})]/[\ln(1-C)(1+ee \text{ of recovery alcohol})]$$

Conversion rate (%)=[ee of recovery alcohol]/[(ee of recovery alcohol)+(ee of generated ester)]

TABLE 1

| No. | Solvent | Dipole moment of solvent/D | Yield (2; 1)/% | ee (2; 1)/% | Ratio of reaction rates (s) |
|---|---|---|---|---|---|
| 1 | Toluene | 0.37 | 45; 47 | 85; 65 | 25 |
| 2 | Diethyl ether | 1.12 | 45; 45 | 83; 67 | 22 |
| 3 | Dichloromethane | 1.14 | 41; 46 | 91; 72 | 44 |
| 4 | Tetrahydrofuran | 1.70 | 42; 42 | 92; 61 | 48 |
| 5 | Ethyl acetate | 1.88 | 46; 40 | 86; 73 | 28 |
| 6 | Acetone | 2.69 | 44; 39 | 89; 71 | 38 |
| 7 | Acetonitrile | 3.44 | 46; 46 | 85; 47 | 20 |
| 8 | DMA[a] | 3.72 | 38; 47 | 94; 13 | 35 |
| 9 | DMF[b] | 3.86 | 39; 42 | 92; 10 | 27 |
| 10 | DMI[c] | 4.07 | 19; 48 | 93; 7 | 28 |
| 11 | NMP[d] | 4.09 | 31; 49 | 92; 12 | 27 |
| 12 | DMSO[e] | 4.30 | 22; 61 | 89; 2 | 18 |

[a] N,N-dimethylacetamide
[b] N,N-dimethylformamide
[c] 1,3-dimethyl-2-imidazolidinone
[d] N-methylpyrrolidone
[e] Dimethyl sulfoxide As understood from Table 1, in Experimental Example 1 using commonly used nonpolar solvents and polar solvents, the ratio of reaction rate s was extremely high at 18 or higher in cases of using either solvent. In the case of using a solvent having a dipole moment less than 3.0, the enantioselectivity of both the generated optically active carboxylic acid ester (2) and unreacted carboxylic acid (1) increased (Nos. 1 to 6). On the other hand, in the case of using a polar solvent having a dipole moment of 3.0 or higher, the enantioselectivity of the generated optically active carboxylic acid ester (2) increased, while the enantioselectivity of the unreacted carboxylic acid (1) lowered, and racemization of the carboxylic acid tended to occur (Nos. 7 to 12). The physical properties of the obtained optically active carboxylic acid ester (2) and unreacted carboxylic acid (1) are as follows.

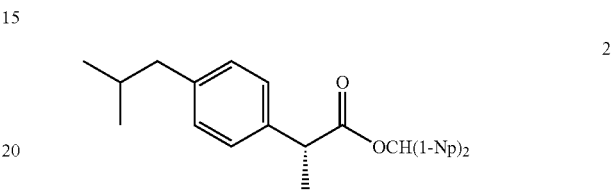

(R)-Ibuprofen di(1-naphthyl)methyl ester ((R)-2) [Table 1, No. 3, 91% ee]

HPLC (CHIRALPAK AD-H, i-PrOH/hexane=1/9, flow rate=0.5 mL/min):
$t_R$=12.6 min (4.7%), $t_R$=23.1 min (95.3%);
IR (neat): 3036, 1735, 1599, 1512, 782, 679 cm$^{-1}$;
$^1$H NMR (CDCl$_3$): δ
8.29 (s, 1H),
8.02-7.93 (m, 1H),
7.85-7.60 (m, 5H),
7.47-7.26 (m, 3H),
7.24-7.02 (m, 6H),
7.00-6.88 (m, 3H),
3.74 (q, J=7.1 Hz, 1H),
2.38 (d, J=7.1 Hz, 2H),
1.78 (tqq, J=7.1, 6.6, 6.6 Hz, 1H),
1.43 (d, J=7.1 Hz, 3H),
0.84 (d, J=6.6 Hz, 6H);
$^{13}$C NMR (CDCl$_3$): δ 173.7, 140.6, 137.2, 134.9, 134.7, 133.8, 133.7, 131.2, 130.9, 129.3, 129.1, 128.8, 128.7, 128.6, 127.5, 126.7, 126.34, 126.25, 125.8, 125.6, 125.2, 125.0, 123.5, 123.4, 70.9, 45.3, 45.0, 30.2, 22.4, 18.1;
HR MS: calcd for C$_{34}$H$_{32}$O$_2$Na (M+Na$^+$) 495.2295. found 495.2276.

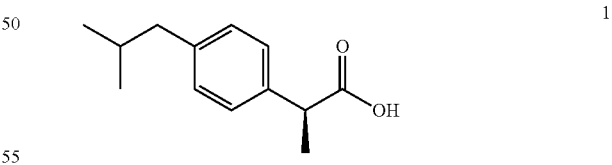

(S)-Ibuprofen ((S)-1) [Table 1, No. 3, 72% ee]
HPLC (CHIRALPAK AD-H, i-PrOH/hexane/TFA=1/100/0.1, flow rate=1.0 mL/min):
$t_R$=30.5 min (86.0%), $t_R$=34.0 min (14.0%);
$^1$H NMR (CDCl$_3$): δ
10.30 (br s, 1H, COOH),
7.14 (d, J=7.9 Hz, 2H),
7.02 (d, J=7.9 Hz, 2H),
3.63 (q, J=7.3 Hz, 1H),
2.37 (q, J=7.3 Hz, 2H),
1.77 (tqq, J=7.3, 6.5, 6.5 Hz, 1H), 1.42 (d, J=7.3 Hz, 3H),
0.82 (d, J=6.5 Hz, 6H);
$^{13}$C NMR (CDCl$_3$): δ 181.0, 140.8, 136.9, 129.4, 127.3, 45.0, 44.9, 30.2, 22.4, 18.1.

Experimental Example 2

Consideration of Reaction Conditions

The reaction conditions were considered in dynamic kinetic resolution by way of asymmetric esterification with ibuprofen (1) as a substrate.

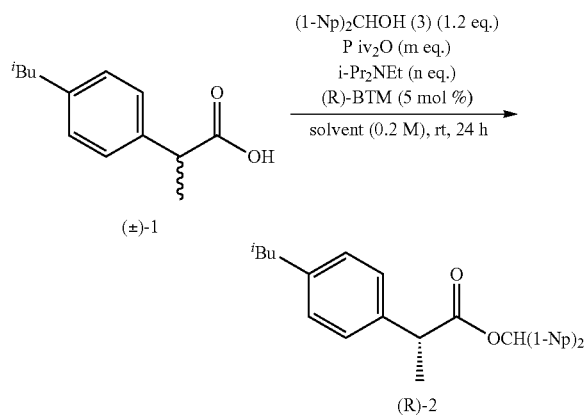

At the reaction conditions shown in Table 2, 1.2 to 4.0 equivalents of pivalic acid anhydride, 1.2 equivalents of di(1-naphthyl)methanol, 0 to 4.8 equivalents of diisopropylethylamine and 5 mol % (+)-benzotetramisole were added to 1 equivalent of ibuprofen in 0.2 moles of N,N-dimethylformamide, and were allowed to react at room temperature according to the chemical equation for 24 hours for Nos. 13 to 18, and for 48 hours for No. 19. After cooling the reaction system to 0° C., 1N hydrochloric acid was added to stop the reaction. After isolating the organic layer, the aqueous layer was extracted with ethyl acetate. After combining the organic layer and drying with anhydrous sodium sulfate, a crude product was obtained by filtering and vacuum concentrating. The generated optically active ester was separated by way of silica gel thin layer chromatography to obtain the target compound.

TABLE 2

| No. | Equivalents of acid anhydride (m) | Equivalents of base (n) | Reaction time/h | Yield of 2/% (ee/%) | Yield of 1/% (ee/%) |
|---|---|---|---|---|---|
| 13 | 4.0 | 0 | 24 | 76 (84) | 9 (76) |
| 14 | 4.0 | 1.2 | 24 | 87 (90) | 9 (34) |
| 15 | 4.0 | 2.0 | 24 | 90 (90) | 6 (30) |
| 16 | 4.0 | 4.8 | 24 | 88 (91) | 6 (7) |
| 17 | 1.2 | 4.8 | 24 | 57 (90) | 24 (13) |
| 18 | 2.4 | 4.8 | 24 | 71 (92) | 16 (7) |
| 19 | 2.4 | 4.8 | 48 | 93 (91) | 4 (12) |

As is understood from Table 2, although diisopropylethylamine was not necessarily required in the progression of reaction (No. 13), when the amount of diisopropylethylamine was great, racemization of the unreacted carboxylic acid tended to occur, and the yield and enantioselectivity of the target optically active carboxylic acid ester (2) increased (Nos. 14 to 16). On the other hand, when the amount of acid anhydride was small, the high enantioselectivity of esterification was maintained; however, the yield declined, and also the racemization of the carboxylic acid (1) did not occur easily (Nos. 17 and 18). However, by lengthening the reaction time (No. 19), it was made so that the optically active carboxylic acid ester (2) that is the target compound could be obtained at high yield and high enantiomeric excess ratio.

Experimental Example 3

Effect of Reaction Solvent (2)

The effect of the solvent was considered in dynamic kinetic resolution by way of asymmetric esterification with ibuprofen as a substrate.

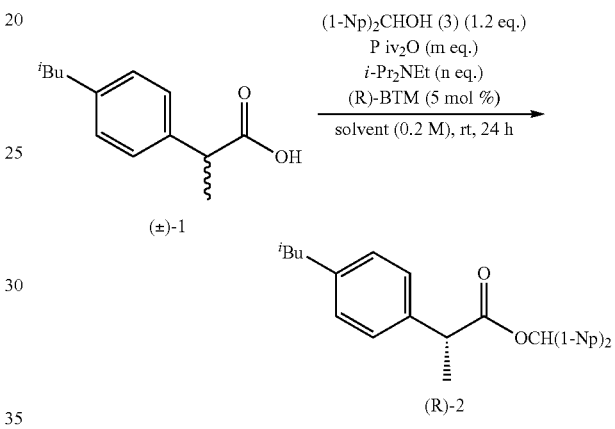

To 1 equivalent of ibuprofen in 0.2 moles of each solvent shown in Table 3, 2.4 equivalents of pivalic acid anhydride, 1.2 equivalents of di(1-naphthyl)methanol, 4.8 equivalents of diisopropylethylamine and 5 mol % (+)-benzotetramisole were added, and were allowed to react at room temperature according to the chemical equation for 48 hours. After cooling the reaction system to 0° C., 1N hydrochloric acid was added to stop the reaction. After isolating the organic layer, the aqueous layer was extracted with ethyl acetate. After combining the organic layer and drying with anhydrous sodium sulfate, a crude product was obtained by filtering and vacuum concentrating. The generated optically active carboxylic ester was separated by way of silica gel thin layer chromatography to obtain the target compound.

TABLE 3

| No. | Solvent | Yield of 2/% (ee/%) | Yield of 1/% (ee/%) |
|---|---|---|---|
| 20 | DMA | 88 (91) | 3 (13) |
| 21 | DMF | 93 (91) | 4 (12) |
| 22 | DMI | 61 (86) | 24 (2) |
| 23 | NMP | 75 (92) | 10 (4) |
| 24 | DMSO | 37 (86) | 43 (−4[a]) |

[a]Absolute configuration of 1 is R

As is understood from Table 3, also in the case of using any of the highly polar solvents, the target optically active carboxylic acid ester (2) was obtained at a high enantiomeric excess ratio. In particular, upon using N,N-dimethylformamide and N,N-dimethylacetamide, the optically active carboxylic acid ester (2) was obtained at high yield and high enantiomeric excess ratio (Nos. 20 and 21).

Experimental Test 4

Effect of Substituent Group on Aromatic Ring of Substrate

The effects of substituent group(s) on the aromatic ring of the substrate were considered in dynamic kinetic resolution by way of asymmetric esterification.
(Standardized Method)

To 1 equivalent of various racemic carboxylic acids 1a to 1i in 0.2 moles of a N,N-dimethylformamide solvent, 2.4 equivalents of pivalic acid anhydride, 1.2 equivalents of di(1-naphthyl)methanol, 4.8 equivalents of diisopropylethylamine and 5 mol % (+)-benzotetramisole were added, and were allowed to react at room temperature in accordance with the chemical equation for 48 hours. After cooling the reaction system to 0° C., 1N hydrochloric acid was added to stop the reaction. After isolating the organic layer, the aqueous layer was extracted with ethyl acetate. After combining the organic layer and drying with anhydrous sodium sulfate, a crude product was obtained by filtering and vacuum concentrating. The generated optically active ester was separated by way of silica gel thin layer chromatography to obtain the target compound.

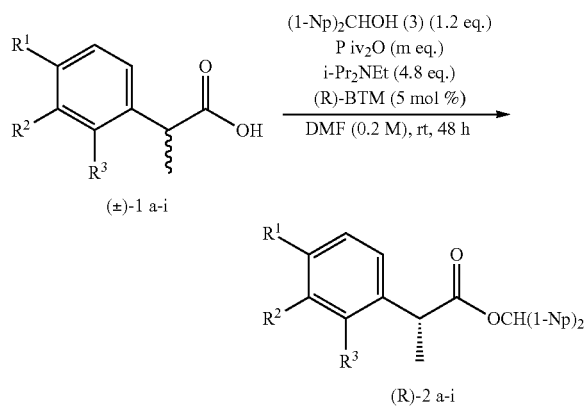

TABLE 4

| No. | R¹ | R² | R³ | Equivalents of acid anhydride (m) | Reaction temperature | Reaction time/h | Yield of 2/% (ee/%) |
|---|---|---|---|---|---|---|---|
| 25 | Me | H | H | 2.4 | rt | 48 | 94 (84) |
| 26 | H | Me | H | 2.4 | rt | 48 | 91 (91) |
| 27 | H | H | Me | 2.4 | rt | 48 | 85 (90) |
| 28 | OMe | H | H | 2.4 | rt | 48 | 76 (87) |
| 29 | OMe | H | H | 4.8 | rt | 72 | 94 (87) |
| 30 | H | OMe | H | 2.4 | rt | 48 | 96 (91) |
| 31 | H | H | OMe | 2.4 | rt | 48 | 50 (97) |
| 32 | H | H | OMe | 4.8 | rt | 72 | 56 (97) |
| 33 | Cl | H | H | 2.4 | rt | 48 | 99 (82) |
| 34 | Cl | H | H | 2.4 | 0° C. | 48 | 99 (87) |
| 35 | H | Cl | H | 2.4 | rt | 48 | 98 (73) |
| 36 | H | Cl | H | 2.4 | 0° C. | 48 | 96 (87) |
| 37 | H | H | Cl | 2.4 | rt | 48 | 89 (80) |
| 38 | H | H | Cl | 2.4 | 0° C. | 48 | 67 (88) |

As is understood from Table 4, irrespective of the electrical effect of the substituent group on the aromatic ring of the substrate and the position thereof, in cases using any of the substrates, the optically active carboxylic acid ester (2) was obtained at high yield and high enantiomeric excess ratio. When there was an electron donating group such as a methoxy group, favorable results were obtained with the amount of acid anhydride being greater and the reaction time being longer than the standardized method (Nos. 29 and 32). When there was an electron accepting group such as a chloryl group, the enantiomeric excess ratio increased with setting the reaction temperature to 0° C. with the standardized method (Nos. 34, 36 and 38). The physical properties of the obtained optically active carboxylic acid ester (2) are as follows.

(No. 25)

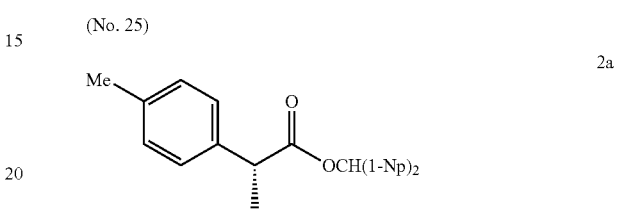

2a

Di(1-naphthyl)methyl(R)-2-(4-methylphenyl)propanoate ((R)-2a) [84% ee]:
HPLC (CHIRALPAK AD-H, i-PrOH/hexane=1/9, flow rate=0.5 mL/min):
$t_R$=14.1 min (8.2%), $t_R$=19.7 min (91.8%);
IR (neat): 3051, 1733, 1598, 1512, 801, 777, 732 cm$^{-1}$;
$^1$H NMR (CDCl$_3$): δ
8.27 (s, 1H),
7.98-7.91 (m, 1H),
7.83-7.76 (m, 1H),
7.72 (t, J=8.2 Hz, 2H),
7.66 (d, J=8.2 Hz, 1H),
7.62 (d, J=8.6 Hz, 1H),
7.44-7.36 (m, 1H),
7.31 (t, J=7.5 Hz, 1H),
7.22-7.14 (m, 2H),
7.13-7.01 (m, 4H),
6.97 (d, J=7.9 Hz, 2H),
6.92 (d, J=7.5 Hz, 1H),
3.72 (q, J=7.0 Hz, 1H),
2.25 (s, 3H),
1.42 (d, J=7.0 Hz, 3H);
$^{13}$C NMR (CDCl$_3$): δ 173.7, 137.0, 136.7, 134.9, 134.6, 133.8, 133.7, 131.2, 130.9, 129.2, 129.1, 128.8, 128.7, 128.6, 128.3, 127.6, 126.7, 126.3, 126.2, 125.8, 125.6, 125.3, 125.2, 125.0, 123.5, 123.3, 71.1, 45.2, 21.0, 18.2;
HR MS: calcd for C$_{31}$H$_{26}$O$_2$Na (M+Na$^+$) 453.1825. found 453.1816.

(No. 26)

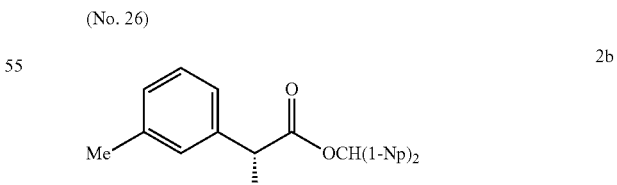

2b

Di(1-naphthyl)methyl(R)-2-(3-methylphenyl)propanoate ((R)-2b) [91% ee]:
HPLC (CHIRALPAK AD-H, i-PrOH/hexane=1/9, flow rate=0.5 mL/min):
$t_R$=14.4 min (4.6%), $t_R$=18.0 min (95.4%);
$^1$H NMR (CDCl$_3$): δ

8.40-8.36 (m, 1H),
8.09-8.00 (m, 1H),
7.92-7.82 (m, 1H),
7.86-7.75 (m, 2H),
7.73 (dd, J=8.4, 8.4 Hz, 1H),
7.54-7.34 (m, 3H),
7.32-7.11 (m, 5H),
7.09-6.98 (m, 4H),
3.88-3.74 (m, 1H),
2.22 (s, 3H),
1.51 (dd, J=6.9, 1.8 Hz, 3H);
$^{13}$C NMR (CDCl$_3$): δ 173.6, 139.9, 138.2, 134.8, 134.5, 133.8, 133.6, 131.2, 130.8, 129.1, 128.8, 128.7, 128.6, 128.4, 128.3, 127.9, 126.7, 126.33, 126.27, 125.8, 125.6, 125.3, 125.2, 125.0, 124.8, 123.5, 123.3, 71.0, 45.5, 21.3, 18.2;
HR MS: calcd for C$_{31}$H$_{26}$O$_2$Na (M+Na$^+$) 453.1825. found 453.1817.
Analytical data on racemic compound: Mp: 120-121° C. (hexane);
IR (KBr): 3055, 2970, 2931, 1597, 1241, 1157, 779, 741, 710 cm$^{-1}$.

(No. 27)

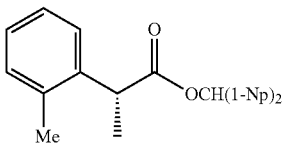

2c

Di(1-naphthyl)methyl(R)-2-(2-methylphenyl)propanoate ((R)-2c) [90% ee]:
HPLC (CHIRALPAK AD-H, i-PrOH/hexane=1/50, flow rate=0.5 mL/min):
$t_R$=21.6 min (4.1%), $t_R$=34.0 min (94.9%);
IR (neat): 3057, 1599, 1510, 752, 730 cm$^{-1}$;
$^1$H NMR (CDCl$_3$):
8.31 (s, 1H),
8.02-7.96 (m, 1H),
7.83-7.78 (m, 1H),
7.73 (t, J=8.0 Hz, 2H),
7.69-7.62 (m, 2H),
7.45-7.39 (m, 2H),
7.34-7.30 (m, 1H),
7.23-7.17 (m, 2H),
7.14-7.00 (m, 6H),
6.88 (d, J=8.0 Hz, 1H),
4.00 (q, J=7.0 Hz, 1H),
2.16 (s, 3H),
1.43 (d, J=7.0 Hz, 3H);
$^{13}$C NMR (CDCl$_3$): δ 173.7, 138.5, 135.9, 134.9, 134.6, 133.8, 133.7, 131.2, 130.9, 130.5, 129.1, 128.9, 128.7, 128.6, 127.0, 126.9, 126.7, 126.34, 126.30, 126.28, 125.8, 125.6, 125.3, 125.2, 125.0, 123.5, 123.4, 71.0, 41.4, 19.7, 17.6;
HR MS: calcd for C$_{31}$H$_{26}$O$_2$Na (M+Na$^+$) 453.1825. found 453.1813.

(No. 28)

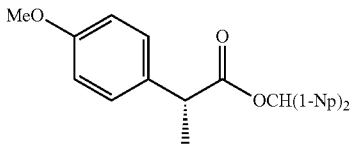

2d

Di(1-naphthyl)methyl(R)-2-(4-methoxyphenyl)propanoate ((R)-2d) [87% ee]:
HPLC (CHIRALPAK AD-H, i-PrOH/hexane=1/9, flow rate=0.5 mL/min):
$t_R$=22.7 min (6.4%), $t_R$=28.8 min (93.6%);
IR (neat): 3059, 1733, 1608, 1512, 783, 733 cm$^{-1}$;
$^1$H NMR (CDCl$_3$):
8.26 (s, 1H),
7.97-7.89 (m, 1H),
7.85-7.58 (m, 5H),
7.46-7.04 (m, 9H),
6.93 (d, J=6.9 Hz, 1H),
6.75-6.67 (m, 2H),
3.78-3.68 (m, 4H),
1.42 (d, J=6.9 Hz, 3H);
$^{13}$C NMR (CDCl$_3$): δ 173.7, 158.7, 134.8, 134.6, 133.8, 133.6, 132.1, 131.2, 130.9, 129.1, 128.83, 128.76, 128.71, 128.6, 128.3, 126.7, 126.3, 126.2, 125.8, 125.6, 125.3, 125.2, 125.0, 123.5, 123.3, 113.9, 71.0, 55.3, 44.8, 18.2;
HR MS: calcd for C$_{31}$H$_{26}$O$_2$Na (M+Na$^+$) 469.1774. found 469.1754.

(No. 30)

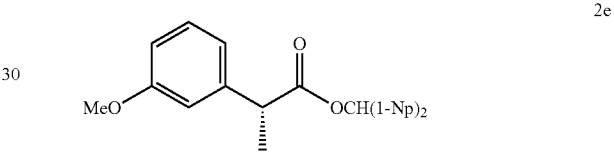

2e

Di(1-naphthyl)methyl(R)-2-(3-methoxyphenyl)propanoate ((R)-2e) [91% ee]:
HPLC (CHIRALPAK AD-H, i-PrOH/hexane=1/9, flow rate=0.5 mL/min):
$t_R$=21.3 min (4.5%), $t_R$=35.6 min (95.5%);
IR (neat): 3055, 2978, 1736, 1597, 1250, 1157, 779, 764, 702 cm$^{-1}$;
$^1$H NMR (CDCl$_3$): δ
8.36 (s, 1H),
8.08-7.98 (m, 1H),
7.92-7.84 (m, 1H),
7.81 (d, J=7.5 Hz, 1H),
7.79 (d, J=8.1 Hz, 1H),
7.75 (d, J=8.1 Hz, 1H),
7.72 (d, J=8.7 Hz, 1H),
7.53-7.43 (m, 2H),
7.40 (dd, J=7.5, 7.5 Hz, 1H),
7.32-7.12 (m, 5H),
7.01 (d, J=6.9 Hz, 1H),
6.87-6.71 (m, 3H),
3.82 (q, J=7.2 Hz, 1H),
3.62 (s, 3H),
1.52 (d, J=7.2 Hz, 3H);
$^{13}$C NMR (CDCl$_3$): δ 173.4, 159.7, 141.4, 134.7, 134.5, 133.8, 133.6, 131.2, 130.8, 129.5, 129.1, 128.8, 128.7, 128.6, 126.7, 126.4, 126.3, 125.8, 125.6, 125.3, 125.2, 125.0, 123.4, 123.3, 120.1, 113.1, 112.9, 71.1, 55.1, 45.6, 18.1;
HR MS: calcd for C$_{31}$H$_{26}$O$_3$Na (M+Na$^+$) 469.1774. found 469.1766.

(No. 31)

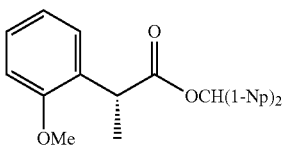

Di(1-naphthyl)methyl(R)-2-(2-methoxyphenyl)propanoate ((R)-2f) [97% ee]:

HPLC (CHIRALPAK AD-H, i-PrOH/hexane=1/9, flow rate=0.5 mL/min):
$t_R$=17.8 min (1.5%), $t_R$=30.0 min (98.5%);
$^1$H NMR (CDCl$_3$): δ
8.35 (s, 1H),
8.13-7.95 (m, 1H),
7.82-7.53 (m, 5H),
7.46-7.32 (m, 3H),
7.30-7.07 (m, 7H),
6.79 (td, J=7.6, 1.2 Hz, 1H),
6.68 (dd, J=8.1, 1.2 Hz, 1H),
4.08 (q, J=7.2 Hz, 1H),
3.39 (s, 3H),
1.42 (d, J=7.2 Hz, 3H);
$^{13}$C NMR (CDCl$_3$): δ 174.1, 156.8, 135.2, 135.0, 133.8, 133.7, 131.2, 131.0, 128.9, 128.8, 128.74, 128.67, 128.61, 128.3, 128.1, 126.6, 126.4, 126.2, 125.8, 125.7, 125.6, 125.14, 125.06, 123.7, 123.6, 120.5, 110.3, 70.8, 55.0, 39.6, 16.8;
HR MS: calcd for C$_{31}$H$_{26}$O$_3$Na (M+Na$^+$) 469.1774. found 469.1770.

Analytical data on racemic compound: Mp: 160-161° C. (CHCl$_3$/petroleum ether); IR (KBr): 3060, 1730, 1600, 1494, 778, 758 cm$^{-1}$.

(No. 34)

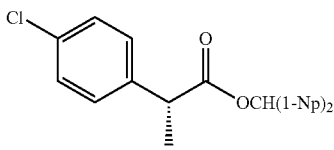

Di(1-naphthyl)methyl(R)-2-(4-chlorophenyl)propanoate ((R)-2g) [87% ee]:

HPLC (CHIRALPAK AD-H, i-PrOH/hexane=1/9, flow rate=0.5 mL/min):
$t_R$=17.9 min (6.6%), $t_R$=20.3 min (93.4%);
IR (neat): 3052, 1737, 1599, 1510, 837, 777 cm$^{-1}$;
$^1$H NMR (CDCl$_3$): δ
8.26 (d, J=3.0 Hz, 1H),
7.90 (dd, J=7.5, 3.0 Hz, 1H),
7.81 (d, J=7.5 Hz, 1H),
7.75 (t, J=8.5 Hz, 2H),
7.70 (d, J=8.0 Hz, 1H),
7.62 (dd, J=8.5, 3.0 Hz, 1H),
7.45-7.32 (m, 3H),
7.26-7.04 (m, 8H),
6.93 (dd, J=7.0, 3.0 Hz, 1H),
3.73 (qd, J=8.5, 1.5 Hz, 1H),
1.45-1.41 (m, 3H);
$^{13}$C NMR (CDCl$_3$): δ 173.1, 138.4, 134.5, 134.4, 133.8, 133.7, 133.0, 131.1, 130.8, 129.2, 129.1, 128.9, 128.7, 128.6, 128.3, 126.7, 126.4, 126.1, 125.9, 125.7, 125.3, 125.2, 124.5, 123.3, 123.2, 71.4, 45.0, 18.0;
HR MS: calcd for C$_{30}$H$_{23}$O$_2$ClNa (M+Na$^+$) 473.1279. found 473.1284.

(No. 36)

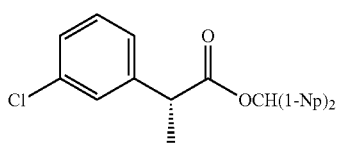

Di(1-naphthyl)methyl(R)-2-(3-chlorophenyl)propanoate ((R)-2h) [87% ee]:

HPLC (CHIRALPAK AD-H, i-PrOH/hexane=1/9, flow rate=0.5 mL/min):
$t_R$=12.7 min (6.3%), $t_R$=16.9 min (93.7%);
IR (neat): 3055, 2978, 1736, 1589, 1242, 1165, 787, 756 cm$^{-1}$;
$^1$H NMR (CDCl$_3$): δ
8.37 (s, 1H),
8.00 (d, J=8.5 Hz, 1H),
7.91-7.87 (m, 1H),
7.82 (dd, J=7.5, 7.5 Hz, 2H),
7.77 (d, J=8.0 Hz, 1H),
7.73 (d, J=8.5 Hz, 1H),
7.52-7.45 (m, 2H),
7.42 (dd, J=7.5, 7.5 Hz, 1H),
7.33-7.27 (m, 2H),
7.26-7.17 (m, 4H),
7.14 (dd, J=7.5, 7.5 Hz, 1H),
7.09 (d, J=7.5 Hz, 1H),
7.04 (d, J=8.0 Hz, 1H),
3.81 (q, J=7.0 Hz, 1H),
1.51 (d, J=7.0 Hz, 3H);
$^{13}$C NMR (CDCl$_3$): δ 172.9, 141.9, 134.6, 134.4, 134.4, 133.8, 133.7, 131.2, 130.9, 129.8, 129.2, 128.9, 128.7, 127.9, 127.4, 126.8, 126.4, 126.2, 126.0, 125.9, 125.8, 125.4, 125.2, 125.0, 123.34, 123.25, 71.4, 45.3, 18.1;
HR MS: calcd for C$_{30}$H$_{23}$ClO$_2$Na (M+Na$^+$) 473.1279. found 473.1298.

(No. 38)

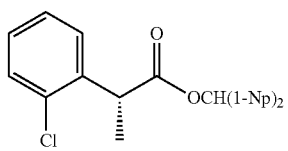

Di(1-naphthyl)methyl(R)-2-(2-chlorophenyl)propanoate ((R)-2i) [88% ee]:

HPLC (CHIRALPAK IC, i-PrOH/hexane=1/50, flow rate=1.0 mL/min):
$t_R$=8.7 min (6.0%), $t_R$=10.8 min (94.0%);
$^1$H NMR (CDCl$_3$): δ
8.35 (s, 1H)
8.12-7.96 (m, 1H)
7.83-7.65 (m, 5H),
7.42-7.38 (m, 2H), 7.34 (t, J=7.5 Hz, 1H)

7.30-7.21 (m, 3H), 7.19-7.12 (m, 3H), 7.10-6.98 (m, 3H), 4.29 (q, J=7.5 Hz, 1H), 1.43 (d, J=7.5 Hz, 3H);

$^{13}$C NMR (CDCl$_3$): δ 173.1, 137.8, 134.8, 134.5, 133.83, 133.81, 133.7, 131.2, 130.9, 129.5, 129.1, 128.9, 128.8, 128.7, 128.5, 128.3, 127.0, 126.7, 126.4, 126.3, 125.8, 125.7, 125.6, 125.2, 125.0, 123.6, 123.4, 71.4, 42.1, 17.4;

HR MS: calcd for C$_{30}$H$_{23}$O$_2$ClNa (M+Na$^+$) 473.1279. found 473.1261.

Analytical data on racemic compound: Mp: 143-144° C. (petroleum ether); IR (KBr): 3067, 1718, 1598, 1509, 795, 764 cm$^{-1}$.

Experimental Example 5

Consideration of Universalness of Substrate

Consideration of the universalness was made in dynamic kinetic resolution according to the asymmetric esterification of substrates 1j-1 to 1j-28 under the optimized conditions of Experimental Example 4.

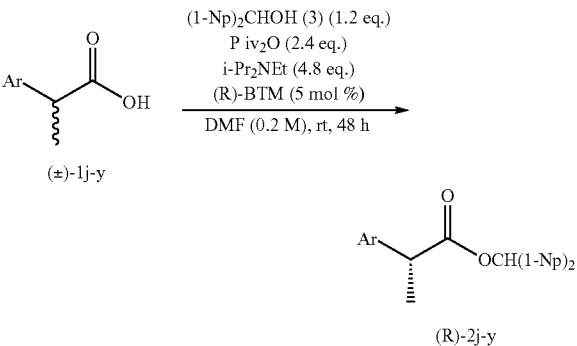

(±)-1j-y (R)-2j-y

TABLE 5

| No. | Ar | Yield of 2/% (ee/%) |
|---|---|---|
| 39 | phenyl | 88 (92) |
| 40 | 1-naphthyl | 95 (91) |
| 41 | 2-naphthyl | 90 (89) |
| 42 | 9-phenanthrenyl | 87 (95) |
| 43 | 5-benzo-1,3-dioxolyl | 95 (87) |
| 44 | 3,4-dimethoxyphenyl | 75 (84) |
| 45 | 3,5-dimethoxyphenyl | 89 (90) |
| 46 | 3,4,5-trimethoxyphenyl | 90 (90) |
| 47 | 3-fluorophenyl | 96 (89)* |
| 48 | 2-fluorophenyl | 89 (93) |
| 49 | 2-bromophenyl | 76 (85) |
| 50 | 2,3-dichlorophenyl | 99 (82) |
| 51 | 2,4-dichlorophenyl | 99 (82) |
| 52 | 3-chloro-4-methoxyphenyl | 96 (85) |
| 53 | 3-benzoylphenyl | 90 (86)* |
| 54 | 3-phenoxyphenyl | 95 (87) |
| 55 | 4-(2-fluoro-1,1'-biphenyl) | 89 (81)* |
| 56 | 6-methoxy-2-naphthyl | 89 (90) |
| 57 | [4-[(2-oxocyclopentyl)methyl]]phenyl | 90 (89) |
| 58 | 7-(5H-chromeno[2,3-b])pyridinyl | 95 (78) |
| 59 | [4-[2-(1-oxoisoindolinyl)]]phenyl | 96 (90) |
| 60 | 3-(6-chloro-9H)carbazoyl | 81 (91) |

TABLE 5-continued

| No. | Ar | Yield of 2/% (ee/%) |
|---|---|---|
| 61 | 3-(6-chloro-9-tert-butyloxycarbonyl)carbazoyl | 88 (87) |
| 62 | 2-thienyl | 97 (91)** |
| 63 | 3-thienyl | 97 (91) |
| 64 | 2-[1-methyl-5-(4-toluyloxy)]pyrrolyl | 96 (97)** |
| 65 | 2-(1-tert-butyloxycarbonyl)indolyl | 99 (87) |
| 66 | 3-(1-tert-butyloxycarbonyl)indolyl | 89 (99) |

*Reaction carried out at 0° C.
**Reaction carried out at 0° C. without adding i-Pr$_2$Net As is understood from Table 5, this reaction is applicable to various substrates, and in every case, the target optically active carboxylic acid ester (2) was obtained at high yield and high enantiomeric excess ratio. The properties of the obtained optically active carboxylic acid esters 2j-1 to 2j-28 are as follows.

(No. 39)

2j

Di(1-naphthyl)methyl(R)-2-phenylpropanoate ((R)-2j-1) [92% ee]:

HPLC (CHIRALPAK AD-H, i-PrOH/hexane=1/50, flow rate=1.0 mL/min):

t$_R$=14.8 min (4.1%), t$_R$=19.8 min (95.9%);

$^1$H NMR (CDCl$_3$): δ

8.29 (s, 1H), 7.99-7.94 (m, 1H), 7.84-7.79 (m, 1H), 7.74 (t, J=7.0 Hz, 2H), 7.68 (d, J=8.0 Hz, 1H), 7.63 (d, J=8.5 Hz, 1H), 7.45-7.38 (m, 2H), 7.35-7.31 (m, 1H), 7.23-7.14 (m, 7H), 7.11 (t, J=7.5 Hz, 1H), 7.06 (d, J=7.5 Hz, 1H), 6.90 (d, J=7.0 Hz, 1H), 3.77 (q, J=7.0 Hz, 1H), 1.45 (d, J=7.0 Hz, 3H);

$^{13}$C NMR (CDCl$_3$): δ 173.5, 140.0, 134.8, 134.6, 133.8, 133.7, 131.2, 130.8, 129.1, 128.9, 128.7, 128.64, 128.57, 127.8, 127.2, 126.7, 126.4, 126.3, 125.9, 125.6, 125.2, 125.0, 123.5, 123.3, 71.1, 45.6, 18.2;

HR MS: calcd for C$_{30}$H$_{24}$O$_2$Na (M+Na$^+$) 439.1669. found 439.1668.

Analytical data on racemic compound: Mp: 128° C. (i-PrOH/hexane); IR (KBr): 3067, 1728, 1600, 1509, 776, 699 cm$^{-1}$.

(No. 40)

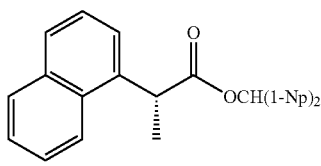

2k

Di(1-naphthyl)methyl(R)-2-(1-naphthyl)propanoate ((R)-2j-2) [91% ee]:
HPLC (CHIRALPAK AD-H, i-PrOH/hexane=1/9, flow rate=0.5 mL/min):
$t_R$=19.0 min (4.3%), $t_R$=32.7 min (95.7%);
$^1$H NMR (CDCl$_3$): δ
8.33 (s, 1H),
7.97-7.83 (m, 2H),
7.83-7.56 (m, 7H),
7.46-6.92 (m, 11H),
6.85 (d, J=7.2 Hz, 1H),
4.54 (q, J=6.9 Hz, 1H),
1.60 (d, J=6.9 Hz, 3H);
$^{13}$C NMR (CDCl$_3$): δ 174.0, 136.0, 134.7, 134.4, 133.9, 133.8, 133.7, 131.4, 131.2, 130.9, 129.0, 128.82, 128.80, 128.7, 128.6, 128.3, 127.8, 126.7, 126.4, 126.22, 126.16, 125.8, 125.7, 125.6, 125.4, 125.1, 124.9, 124.8, 123.5, 123.4, 123.3, 71.3, 41.6, 17.9;
HR MS: calcd for C$_{34}$H$_{26}$O$_2$Na (M+Na$^+$) 489.1825. found 489.1809.
Analytical data on racemic compound: Mp: 152-153° C. (CHCl$_3$/petroleum ether); IR (KBr): 3055, 1735, 1599, 1494, 778, 757 cm$^{-1}$.

(No. 41)

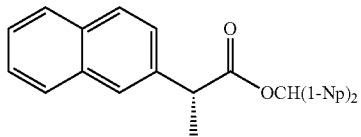

2l

Di(1-naphthyl)methyl(R)-2-(2-naphthyl)propanoate ((R)-2j-3) [89% ee]:
HPLC (CHIRALPAK AD-H, i-PrOH/hexane=1/9, flow rate=0.5 mL/min):
$t_R$=25.3 min (5.6%), $t_R$=53.0 min (94.4%);
IR (neat): 3060, 1737, 1599, 1509, 755 cm$^{-1}$;
$^1$H NMR (CDCl$_3$): δ
8.30 (s, 1H),
7.95 (d, J=7.6 Hz, 1H),
7.86-7.52 (m, 8H),
7.45-7.31 (m, 4H),
7.30-7.11 (m, 4H),
7.10-7.00 (m, 2H),
6.92 (dd, J=7.8, 7.5 Hz, 1H),
6.87 (dd, J=8.1, 6.9 Hz, 1H),
3.92 (q, J=6.9 Hz, 1H),
1.53 (d, J=6.9 Hz, 3H);
$^{13}$C NMR (CDCl$_3$): δ 173.5, 137.5, 134.7, 134.5, 133.8, 133.6, 133.4, 132.6, 131.2, 130.8, 129.1, 128.8, 128.7, 128.6, 128.3, 128.2, 127.8, 127.5, 126.7, 126.4, 126.3, 126.04, 125.98, 125.84, 125.77, 125.6, 125.3, 125.2, 125.0, 123.4, 123.3, 71.3, 45.8, 18.3;

HR MS: calcd for C$_{34}$H$_{26}$O$_2$Na (M+Na$^+$) 489.1825. found 489.1815.

(No. 42)

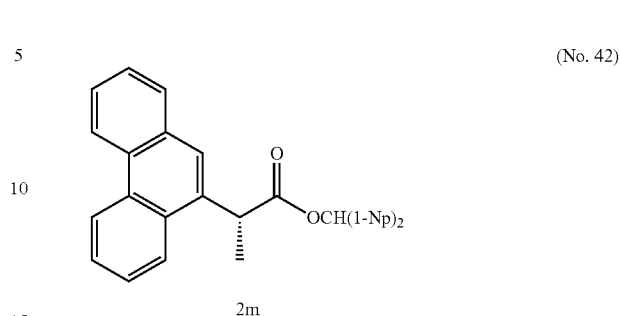

2m

Di(1-naphthyl)methyl(R)-2-(9-phenanthrenyl)propanoate ((R)-2j-4) [95% ee]:
HPLC (CHIRALPAK IC, i-PrOH/hexane=1/50, flow rate=1.0 mL/min):
$t_R$=14.7 min (2.6%), $t_R$=23.9 min (97.4%);
$^1$H NMR (CDCl$_3$): δ
8.62 (d, J=8.4 Hz, 1H),
8.55 (d, J=8.1 Hz, 1H),
8.38 (s, 1H),
7.79-7.87 (m, 2H),
7.82-7.22 (m, 14H),
7.20-7.05 (m, 2H),
7.01-6.90 (m, 3H),
4.54 (q, J=6.9 Hz, 1H),
1.66 (d, J=6.9 Hz, 3H);
$^{13}$C NMR (CDCl$_3$): δ 174.0, 134.6, 134.4, 134.3, 133.8, 133.7, 131.4, 131.2, 130.9, 130.8, 130.7, 130.4, 129.9, 129.0, 128.83, 128.76, 128.6, 128.3, 126.8, 126.7, 126.6, 126.4, 126.3, 126.2, 125.82, 125.80, 125.72, 125.65, 125.1, 125.0, 123.9, 123.5, 123.3, 123.2, 122.3, 71.4, 42.0, 17.8;
HR MS: calcd for C$_{38}$H$_{28}$O$_2$Na (M+Na$^+$) 539.1982. found 539.1968.
Analytical data on racemic compound: Mp: 115-117° C. (CHCl$_3$/petroleum ether); IR (KBr): 3058, 1733, 1599, 1509, 779, 747, 726 cm$^{-1}$.

(No. 43)

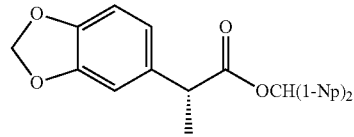

2n

Di(1-naphthyl)methyl(R)-2-(5-benzo[d][1,3]dioxolyl)propanoate ((R)-2j-5) [87% ee]:
HPLC (CHIRALPAK AD-H, i-PrOH/hexane=1/9, flow rate=1.0 mL/min):
$t_R$=15.1 min (6.4%), $t_R$=31.1 min (93.6%);
IR (neat): 3055, 2978, 1728, 1242, 1157, 1041, 787, 733 cm$^{-1}$;
$^1$H NMR (CDCl$_3$): δ
8.34 (s, 1H),
8.00 (d, J=8.5 Hz, 1H),
7.91-7.86 (m, 1H),
7.82 (dd, J=8.0, 8.0 Hz, 2H),
7.77 (d, J=8.0 Hz, 1H),
7.72 (d, J=9.0 Hz, 1H),
7.48 (dddd, J=15.0, 7.5, 7.5, 2.0 Hz, 2H), 7.44-7.38 (m, 1H),
7.33-7.27 (m, 2H),
7.25 (dd, J=8.0, 8.0 Hz, 1H),
7.19 (d, J=7.5 Hz, 1H),
7.08 (d, J=7.5 Hz, 1H),
6.74-6.72 (m, 1H),
6.69-6.67 (m, 1H),
5.90 (s, 2H),
3.75 (q, J=7.0 Hz, 1H),
1.48 (d, J=7.0 Hz, 3H);
$^{13}$C NMR (CDCl$_3$): δ 173.5, 147.7, 146.7, 134.7, 134.5, 133.8, 133.74, 133.69, 131.2, 130.9, 129.1, 128.84, 128.81, 128.6, 126.7, 126.3, 126.2, 125.8, 125.6, 125.4, 125.2, 125.0, 123.5, 123.3, 120.1, 108.20, 108.16, 100.9, 71.2, 45.2, 18.2;
HR MS: calcd for C$_{31}$H$_{24}$O$_4$Na (M+Na$^+$) 483.1567. found 483.1574.

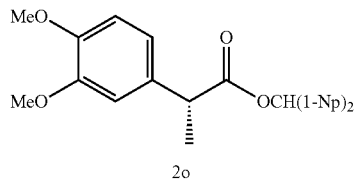

(No. 44)

Di(1-naphthyl)methyl(R)-2-(3,4-dimethoxyphenyl)propanoate ((R)-2j-6) [84% ee]:
HPLC (CHIRALPAK AD-H, i-PrOH/hexane=1/4, flow rate=0.5 mL/min):
t$_R$=17.6 min (8.1%), t$_R$=19.7 min (91.9%);
IR (neat): 3055, 2939, 1728, 1597, 1258, 1158, 787, 733 cm$^{-1}$;
$^1$H NMR (CDCl$_3$): δ
8.35 (s, 1H),
8.01 (d, J=7.5 Hz, 1H),
7.92-7.85 (m, 1H),
7.83 (d, J=7.2 Hz, 1H),
7.81 (d J=7.5 Hz, 1H),
7.76 (d, J=8.1 Hz, 1H),
7.70 (d, J=8.7 Hz, 1H),
7.54-7.37 (m, 3H),
7.33-7.14 (m, 4H),
7.03 (d, J=7.2 Hz, 1H),
6.82-6.71 (m, 2H),
6.67 (d, J=1.5 Hz, 1H),
3.87 (s, 3H),
3.79 (q, J=6.9 Hz, 1H),
3.58 (s, 3H),
1.52 (d, J=6.9 Hz, 3H);
$^{13}$C NMR (CDCl$_3$): δ 173.6, 148.8, 148.1, 134.7, 134.5, 133.8, 133.6, 132.4, 131.1, 130.8, 129.1, 128.8, 128.7, 128.6, 126.7, 126.3, 126.2, 125.8, 125.7, 125.3, 125.2, 125.0, 123.4, 123.3, 119.8, 111.0, 110.5, 71.1, 55.9, 55.6, 45.2, 18.2;
HR MS: calcd for C$_{32}$H$_{28}$O$_4$Na (M+Na$^+$) 499.1880. found 499.1877.

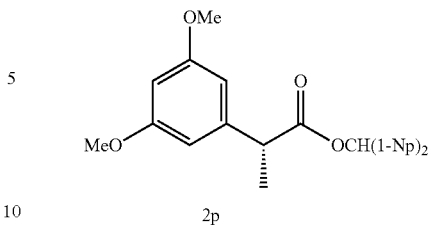

(No. 45)

Di(1-naphthyl)methyl(R)-2-(3,5-dimethoxyphenyl)propanoate ((R)-2j-7) [90% ee]:
HPLC (CHIRALPAK AD-H, i-PrOH/hexane=1/4, flow rate=0.5 mL/min):
t$_R$=14.8 min (5.0%), t$_R$=18.2 min (95.0%);
IR (neat): 3055, 2939, 1736, 1604, 1157, 1057, 787, 741 cm$^{-1}$;
$^1$H NMR (CDCl$_3$): δ
8.37 (s, 1H),
8.03 (d, J=8.0 Hz, 1H),
7.92-7.86 (m, 1H),
7.82 (dd, J=9.0, 9.0 Hz, 2H),
7.77 (d, J=8.5 Hz, 1H),
7.73 (d, J=8.5 Hz, 1H),
7.53-7.44 (m, 2H),
7.42 (dd, J=7.5, 7.5 Hz, 1H),
7.33-7.20 (m, 3H),
7.18 (d, J=7.0 Hz, 1H),
7.07 (d, J=7.0 Hz, 1H),
6.38-6.34 (m, 3H),
3.78 (q, J=7.0 Hz, 1H),
3.62 (s, 6H),
1.51 (d, J=7.0 Hz, 3H);
$^{13}$C NMR (CDCl$_3$): δ 173.2, 160.8, 142.2, 134.7, 134.5, 133.8, 133.7, 131.2, 130.9, 129.1, 128.9, 128.7, 128.6, 126.7, 126.4, 126.3, 125.9, 125.7, 125.4, 125.2, 125.0, 123.5, 123.3, 105.6, 99.6, 71.2, 55.2, 45.9, 18.1;
HR MS: calcd for C$_{32}$H$_{28}$O$_4$Na (M+Na$^+$) 499.1880. found 499.1886.

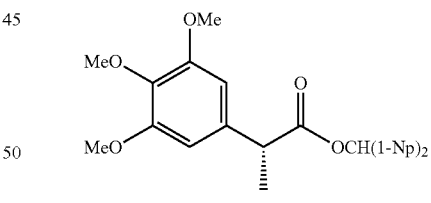

(No. 46)

Di(1-naphthyl)methyl(R)-2-(3,4,5-trimethoxyphenyl)propanoate ((R)-2j-8) [90% ee]:
HPLC (CHIRALPAK AD-H, i-PrOH/hexane=1/4, flow rate=0.5 mL/min):
t$_R$=14.9 min (5.2%), t$_R$=17.7 min (94.8%);
$^1$H NMR (CDCl$_3$): δ
8.37 (s, 1H),
8.01 (d, J=8.0 Hz, 1H),
7.90 (d, J=7.0 Hz, 1H),
7.83 (dd, J=8.5, 8.5 Hz, 2H),
7.78 (d, J=8.0 Hz, 1H),
7.71 (d, J=8.5 Hz, 1H),
7.55-7.44 (m, 2H), 7.43 (dd, J=7.5, 7.5 Hz, 1H),
7.35-7.22 (m, 3H),
7.18 (d, J=7.0 Hz, 1H),
7.06 (d, J=7.0 Hz, 1H),
6.42-6.37 (m, 2H),
3.85 (s, 3H),
3.82-3.75 (m, 1H),
3.62 (s, 6H),
1.53 (d, J=7.0 Hz, 3H);

$^{13}$C NMR (CDCl$_3$): δ 173.3, 153.2, 135.5, 135.5, 134.6, 134.5, 133.8, 133.7, 131.2, 130.9, 129.2, 128.9, 128.8, 128.7, 126.7, 126.4, 126.3, 125.9, 125.7, 125.4, 125.2, 125.0, 123.5, 123.3, 104.6, 71.3, 60.8, 55.9, 45.9, 18.1;

HR MS: calcd for C$_{33}$H$_{30}$O$_5$Na (M+Na$^+$) 529.1985. found 529.1964.

Analytical data on racemic compound: Mp: 85-86° C. (CHCl$_3$/petroleum ether); IR (KBr): 3055, 2939, 1728, 1589, 1242, 1134, 787 cm$^{-1}$.

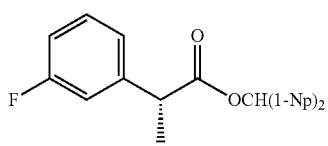

(No. 47)

Di(1-naphthyl)methyl(R)-2-(3-fluorophenyl)propanoate ((R)-2j-9) [89% ee]:

HPLC (CHIRALPAK AD-H, i-PrOH/hexane=1/9, flow rate=0.5 mL/min):

t$_R$=12.3 min (5.4%), t$_R$=15.2 min (94.6%);

IR (neat): 3055, 2978, 1728, 1604, 1257, 1157, 1072, 779, 756, 694 cm$^{-1}$;

$^1$H NMR (CDCl$_3$): δ
8.37 (s, 1H),
8.01 (d, J=8.0 Hz, 1H),
7.89 (d, J=8.0 Hz, 1H),
7.83 (dd, J=8.0, 8.0 Hz, 2H),
7.77 (d, J=8.5 Hz, 1H),
7.73 (d, J=8.5 Hz, 1H),
7.53-7.45 (m, 2H),
7.44-7.39 (m, 1H),
7.32 (d, J=7.5 Hz, 1H),
7.29 (d, J=7.5 Hz, 1H),
7.25-7.16 (m, 3H),
7.00-6.91 (m, 4H),
3.84 (q, J=7.0 Hz, 1H),
1.52 (d, J=7.0 Hz, 3H);

$^{13}$C NMR (CDCl$_3$): δ 172.9, 162.8 (d, J=246.3 Hz), 142.3 (d, J=7.5 Hz), 134.6, 134.4, 133.8, 133.7, 131.1, 130.8, 130.0 (d, J=8.1 Hz), 129.2, 128.9, 128.9, 128.7, 126.7, 126.4, 126.1, 125.9, 125.7, 125.3, 125.2, 125.0, 123.50, 123.47, 123.3 (d, J=7.5 Hz), 114.7 (d, J=21.8 Hz), 114.1 (d, J=21.2 Hz), 71.3, 45.3, 18.0;

HR MS: calcd for C$_{30}$H$_{23}$FO$_2$Na (M+Na$^+$) 457.1574. found 457.1581.

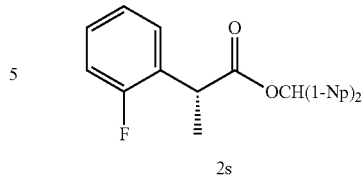

(No. 48)

Di(1-naphthyl)methyl(R)-2-(2-fluorophenyl)propanoate ((R)-2j-10) [93% ee]:

HPLC (CHIRALPAK AD-H, i-PrOH/hexane=1/9, flow rate=0.5 mL/min):

t$_R$=14.7 min (3.7%), t$_R$=18.5 min (96.3%);

$^1$H NMR (CDCl$_3$): δ
8.42 (s, 1H),
8.09-8.04 (m, 1H),
7.91-7.86 (m, 1H),
7.85-7.79 (m, 3H),
7.77 (d, J=8.5 Hz, 1H),
7.52-7.47 (m, 2H),
7.42 (dd, J=8.0, 8.0 Hz, 1H),
7.33 (dd, J=8.0, 8.0 Hz, 1H),
7.31 (dd, J=8.0, 8.0 Hz, 1H),
7.27-7.16 (m, 4H),
7.13 (d, J=7.0 Hz, 1H),
7.03-6.96 (m, 2H),
4.18 (q, J=7.5 Hz, 1H),
1.52 (d, J=7.5 Hz, 3H);

$^{13}$C NMR (CDCl$_3$): δ 173.0, 160.4 (d, J=246.0 Hz), 134.8, 134.6, 133.8, 133.7, 131.2, 130.9, 129.1, 128.84 (d, J=7.3 Hz), 128.81, 128.78, 128.70 (d, J=6.3 Hz), 128.67, 127.3 (d, J=14.4 Hz), 126.7, 126.4, 126.2, 125.9, 125.7, 125.4, 125.2, 125.0, 124.1 (d, J=3.1 Hz), 123.5, 123.4, 115.4 (d, J=22.7 Hz), 38.4 (d, J=2.0 Hz), 17.3;

HR MS: calcd for C$_{30}$H$_{23}$FO$_2$Na (M+Na$^+$) 457.1574. found 457.1555.

Analytical data on racemic compound: MP: 127-128° C. (hexane);

IR (KBr): 3062, 1736, 1188, 1157, 779 cm$^{-1}$.

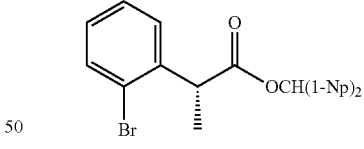

(No. 49)

Di(1-naphthyl)methyl(R)-2-(2-bromophenyl)propanoate ((R)-2j-11) [85% ee]:

HPLC (CHIRALPAK AD-H, i-PrOH/hexane=1/9, flow rate=0.5 mL/min):

t$_R$=15.1 min (7.6%), t$_R$=17.6 min (92.4%);

$^1$H NMR (CDCl$_3$): δ
8.43 (s, 1H),
8.12-8.05 (m, 1H),
7.91-7.85 (m, 2H),
7.86 (d, J=8.5 Hz, 1H),
7.82 (d, J=8.0 Hz, 1H),
7.76 (d, J=8.5 Hz, 1H),
7.53-7.47 (m, 3H),
7.44-7.40 (m, 1H), 7.36-7.30 (m, 2H),
7.28-7.20 (m, 3H),
7.17 (d, J=7.0 Hz, 1H),
7.14 (ddd, J=7.5, 7.5, 1.0 Hz, 1H),
7.06 (ddd, J=7.5, 7.5, 2.0 Hz, 1H),
4.37 (q, J=7.0 Hz, 1H),
1.51 (d, J=7.0 Hz, 3H);
$^{13}$C NMR (CDCl$_3$): δ 173.0, 139.5, 134.7, 134.5, 133.8, 133.7, 131.2, 130.9, 129.1, 128.9, 128.8, 128.7, 128.6, 127.6, 126.7, 126.4, 126.3, 125.8, 125.70, 125.65, 125.2, 125.0, 124.5, 123.6, 123.4, 71.4, 44.7, 17.7;
HR MS: calcd for C$_{30}$H$_{23}$BrO$_2$Na (M+Na$^+$) 517.0774. found 517.0781.
Analytical data on racemic compound: Mp: 138-139° C. (CHCl$_3$/petroleum ether); IR (KBr): 3055, 1188, 787 cm$^{-1}$.

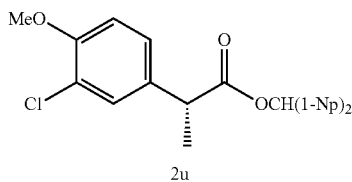

(No. 50)

2u

Di(1-naphthyl)methyl(R)-2-(2,3-dichlorophenyl)propanoate ((R)-2j-12) [82% ee]:
HPLC (CHIRALPAK IC, i-PrOH/hexane=1/50, flow rate=0.5 mL/min):
t$_R$=19.0 min (9.2%), t$_R$=23.2 min (90.8%);
$^1$H NMR (CDCl$_3$): δ
8.32 (s, 1H),
7.98-7.90 (m, 1H),
7.84-7.67 (m, 5H),
7.45-7.32 (m, 3H),
7.31-7.14 (m, 5H),
7.09 (dd, J=7.5, 1.8 Hz, 1H),
7.03 (dd, J=7.8, 1.8 Hz, 1H),
6.94 (dd, J=7.8, 7.5 Hz, 1H),
4.30 (q, J=7.2 Hz, 1H),
1.43 (d, J=7.2 Hz, 3H);
$^{13}$C NMR (CDCl$_3$): δ
172.7, 140.1, 134.6, 134.3, 133.8, 133.7, 133.2, 131.1, 130.9, 129.2, 129.0, 128.9, 128.7, 128.3, 127.5, 127.2, 126.7, 126.6, 126.52, 126.45, 126.2, 125.9, 125.8, 125.2, 125.0, 123.5, 123.3, 71.7, 43.1, 17.4;
HR MS: calcd for C$_{30}$H$_{22}$O$_2$C1$_2$Na (M+Na$^+$) 507.0889. found 507.0887.
Analytical data on racemic compound: MP: 151-154° C. (petroleum ether); IR (KBr): 3059, 1737, 1598, 1510, 1158, 778 cm$^{-1}$.

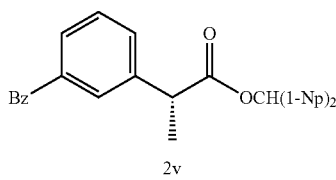

(No. 51)

2v

Di(1-naphthyl)methyl(R)-2-(2,4-dichlorophenyl)propanoate ((R)-2j-13) [82% ee]:
HPLC (CHIRALPAK AD-H, i-PrOH/hexane=1/9, flow rate=0.5 mL/min):
t$_R$=13.6 min (8.9%), t$_R$=18.3 min (91.1%);
$^1$H NMR (CDCl$_3$): δ
8.35 (s, 1H),
8.01-7.92 (m, 1H),
7.84-7.65 (m, 5H),
7.44-7.32 (m, 2H),
7.29-7.16 (m, 6H),
7.14-7.09 (m, 1H),
7.04 (d, J=8.4 Hz, 1H),
6.97 (dd, J=8.4, 1.8 Hz, 1H),
4.35 (q, J=7.2 Hz, 1H),
1.42 (d, J=7.2 Hz, 3H);
$^{13}$C NMR (CDCl$_3$): δ
172.7, 136.3, 134.50, 134.45, 134.3, 133.8, 133.7, 133.4, 131.1, 130.9, 129.33, 129.26, 129.18, 129.0, 128.9, 128.7, 127.2, 126.7, 126.4, 126.2, 125.9, 125.74, 125.70, 125.2, 125.0, 123.5, 123.3, 71.7, 41.7, 17.3;
HR MS: calcd for C$_{30}$H$_{22}$O$_2$C1$_2$Na (M+Na$^+$) 507.0889. found 507.0896.
Analytical data on racemic compound: IR (neat): 3060, 1733, 1590, 1510, 1474, 1156, 777 cm$^{-1}$.

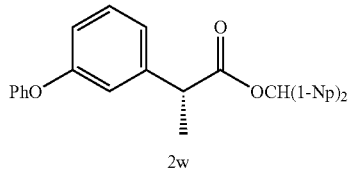

(No. 52)

2w

Di(1-naphthyl)methyl(R)-2-(3-chloro-4-methoxyphenyl)propanoate ((R)-2j-14) [85% ee]:
HPLC (CHIRALPAK AD-H, i-PrOH/hexane=1/9, flow rate=1.0 mL/min):
t$_R$=11.0 min (7.6%), t$_R$=13.4 min (92.4%);
IR (neat): 3055, 2978, 1736, 1597, 1242, 1157, 1080, 779, 741, 694 cm$^{-1}$;
$^1$H NMR (CDCl$_3$): δ
8.34 (s, 1H),
7.97 (d, J=8.1 Hz, 1H),
7.93-7.85 (m, 1H),
7.83 (d, J=7.2 Hz, 1H),
7.81 (d, J=8.1 Hz, 1H),
7.77 (d, J=8.1 Hz, 1H),
7.72 (d, J=8.7 Hz, 1H),
7.54-7.37 (m, 3H),
7.36-7.16 (m, 5H),
7.11-6.99 (m, 2H),
6.73 (d, J=8.4 Hz, 1H),
3.85 (s, 3H),
3.76 (q, J=6.9 Hz, 1H),
1.49 (d, J=6.9 Hz, 3H);
$^{13}$C NMR (CDCl$_3$): δ 173.2, 154.1, 134.6, 134.4, 133.8, 133.7, 133.0, 131.1, 130.8, 129.4, 129.1, 128.9, 128.8, 128.7, 127.0, 126.7, 126.4, 126.1, 125.8, 125.7, 125.4, 125.2, 125.0, 123.4, 123.3, 122.3, 111.9, 71.4, 56.1, 44.5, 18.1;
HR MS: calcd for C$_{31}$H$_{25}$ClO$_3$Na (M+Na$^+$) 503.1384. found 503.1387.

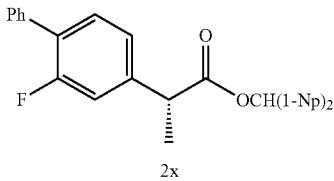

(No. 53)

2x (R)-Ketoprofen di(1-naphthyl)methyl ester ((R)-2j-15) [86% ee]:

HPLC (CHIRALPAK AD-H, i-PrOH/hexane=1/4, flow rate=1.0 mL/min):

$t_R$=13.9 min (6.9%), $t_R$=35.8 min (93.1%);

IR (neat): 3035, 1735, 1660, 1599, 1511, 780, 680 cm$^{-1}$;

$^1$H NMR (CDCl$_3$): δ

8.28 (s, 1H),
7.93-7.85 (m, 1H),
7.82-7.54 (m, 6H),
7.52-7.44 (m, 2H),
7.44-7.06 (m, 13H),
6.95 (d, J=7.1 Hz, 1H),
3.81 (q, J=7.1 Hz, 1H),
1.46 (d, J=7.1 Hz, 3H);

$^{13}$C NMR (CDCl$_3$): δ 196.3, 173.0, 140.1, 137.8, 137.3, 134.5, 134.4, 133.8, 133.7, 132.4, 131.6, 131.1, 130.8, 129.9, 129.5, 129.2, 128.93, 128.91, 128.86, 128.7, 128.6, 128.3, 128.2, 126.7, 126.4, 126.1, 125.9, 125.7, 125.4, 125.2, 125.0, 123.2, 71.4, 45.5, 17.9;

HR MS: calcd for C$_{37}$H$_{28}$O$_3$Na (M+Na$^+$) 543.1931. found 543.1910.

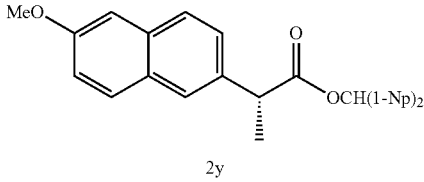

(No. 54)

2y (R)-Fenoprofen Di(1-naphthyl)methyl ester ((R)-2j-16) [87% ee]:

HPLC (CHIRALPAK AD-H, i-PrOH/hexane=1/50, flow rate=1.0 mL/min):

$t_R$=21.0 min (6.7%), $t_R$=25.2 min (93.3%);

IR (neat): 3036, 1735, 1585, 1484, 781, 679 cm$^{-1}$;

$^1$H NMR (CDCl$_3$): δ

8.28 (s, 1H),
7.92 (d, J=8.0 Hz, 1H),
7.82-7.62 (m, 5H),
7.43-7.30 (m, 3H),
7.27-7.09 (m, 7H),
6.98-6.91 (m, 3H),
6.86-6.83 (m, 1H),
6.82-6.73 (m, 3H),
3.72 (q, J=7.0 Hz, 1H),
1.42 (d, J=7.0 Hz, 3H);

$^{13}$C NMR (CDCl$_3$): δ 173.1, 157.3, 157.0, 141.9, 134.7, 134.6, 133.8, 133.7, 131.2, 130.9, 129.8, 129.7, 129.1, 128.9, 128.8, 128.7, 128.3, 126.7, 126.4, 126.1, 125.9, 125.7, 125.3, 125.2, 125.1, 123.4, 123.3, 123.1, 122.6, 118.7, 118.4, 117.6, 71.2, 45.5, 17.9;

HR MS: calcd for C$_{36}$H$_{28}$O$_3$Na (M+Na$^+$) 531.1931. found 531.1948.

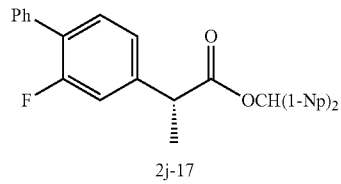

(No. 55)

2j-17

(R)-Flurbiprofen di(1-naphthyl)methyl ester ((R)-2j-17) [81% ee]:

HPLC (CHIRALPAK AD-H, i-PrOH/hexane=1/9, flow rate=0.75 mL/min):

$t_R$=10.8 min (9.5%), $t_R$=17.7 min (90.5%);

IR (neat): 3035, 1734, 1599, 1513, 783, 679 cm$^{-1}$;

$^1$H NMR (CDCl$_3$): δ

8.29 (s, 1H),
7.95-7.86 (m, 1H),
7.80-7.72 (m, 1H),
7.70 (d, J=8.1 Hz, 2H),
7.64 (d, J=8.1 Hz, 2H),
7.46-7.04 (m, 13H),
7.01-6.90 (m, 3H),
3.74 (q, J=7.0 Hz, 1H),
1.44 (t, J=7.0 Hz, 3H);

$^{13}$C NMR (CDCl$_3$): δ 172.9, 159.6 (d, J=248.2 Hz), 141.3, 141.2, 135.5, 134.6, 134.4, 133.8, 133.7, 131.1, 130.9, 130.7 (d, J=3.7 Hz), 129.2, 128.9 (d, J=3.2 Hz), 128.7, 128.5, 128.3, 127.8 (d, J=13.7 Hz), 127.7, 126.7, 126.4, 126.1, 125.9, 125.7, 125.4, 125.2, 125.0, 123.8 (d, J=3.1 Hz), 123.4, 123.3, 115.4 (d, J=23.6 Hz), 71.5, 45.1, 17.9;

HR MS: calcd for C$_{36}$H$_{27}$O$_2$FNa (M+Na$^+$) 533.1887. found 533.1865.

(No. 56)

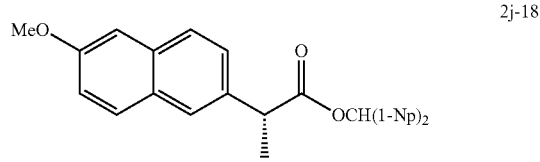

2j-18

(R)-Naproxen di(1-naphthyl)methyl ester ((R)-2j-18) [90% ee]:

HPLC (CHIRALPAK AD-H, i-PrOH/hexane=1/9, flow rate=1.0 mL/min):

$t_R$=13.1 min (5.1%), $t_R$=16.5 min (94.9%);

IR (neat): 3034, 1733, 1604, 1508, 782, 679 cm$^{-1}$;

$^1$H NMR (CDCl$_3$): δ

8.29 (s, 1H),
8.00-7.90 (m, 1H),
7.82-6.96 (m, 17H),
6.95-6.81 (m, 2H),
3.86 (q, J=7.0 Hz, 1H),
3.79 (s, 3H)
1.49 (d, J=7.0 Hz, 3H);

$^{13}$C NMR (CDCl$_3$): δ 173.6, 157.6, 135.1, 134.7, 134.5, 133.8, 133.7, 133.6, 131.2, 130.8, 129.3, 129.1, 128.9, 128.8, 128.7, 128.6, 128.3, 127.1, 126.7, 126.5, 126.3, 126.2, 125.8, 125.6, 125.3, 125.2, 125.0, 123.4, 123.3, 118.9, 105.5, 71.2, 55.2, 45.5, 18.3;

(No. 57)

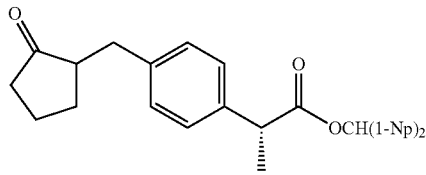

2j-19

(R)-Loxoprofen di(1-naphthyl)methyl ester ((R)-2j-19) [89% ee]:

HPLC (CHIRALPAK IA, i-PrOH/hexane=1/9, flow rate=0.5 mL/min):

$t_R$=23.5 min (94.4%), $t_R$=28.3 min (5.6%);

$^1$H NMR (CDCl$_3$): δ

8.36 (s, 1H),
8.06-7.97 (m, 1H),
7.95-7.86 (m, 1H),
7.82 (dd, J=8.1, 4.2 Hz, 2H),
7.76 (dd, J=8.9, 8.9 Hz, 2H),
7.55-7.37 (m, 3H),
7.34-7.12 (m, 6H),
7.08-6.98 (m, 3H),
3.82 (q, J=7.2 Hz, 1H),
3.14 (ddd, J=13.7, 3.3, 3.3 Hz, 1H),
2.51 (ddd, J=13.7, 10.2, 3.3 Hz, 1H),
2.42-2.25 (m, 2H),
2.19-1.88 (m, 3H),
1.83-1.64 (m, 1H),
1.51 (d, J=7.2 Hz, 3H);

$^{13}$C NMR (CDCl$_3$): δ

220.0, 173.5, 138.90, 138.88, 137.8, 134.8, 134.6, 133.8, 133.7, 131.18, 131.17, 130.9, 129.1, 129.0, 128.8, 128.7, 128.6, 127.8, 126.68, 126.67, 126.3, 126.2, 126.1, 125.8, 125.63, 125.61, 125.29, 125.26, 125.2, 124.9, 123.5, 123.34, 123.32, 71.05, 71.04, 51.0, 45.2, 38.2, 35.2, 35.1, 29.2, 29.1, 20.5, 18.13, 18.11;

HR MS: calcd for C$_{36}$H$_{32}$O$_3$Na (M+Na$^+$) 535.2244. found 535.2232.

Analytical data on racemic compound: IR (neat): 2970, 1736, 1597, 1450, 779, 756 cm$^{-1}$.

(No. 58)

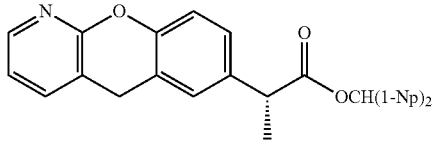

2j-20

(R)-Pranoprofen di(1-naphthyl)methyl ester ((R)-2j-20) [78% ee]:

HPLC (CHIRALPAK AD-H, i-PrOH/hexane=1/4, flow rate=1.0 mL/min):

$t_R$=16.4 min (89.2%), $t_R$=19.6 min (10.8%);

$^1$H NMR (CDCl$_3$): δ

8.35 (s, 1H),
8.23-8.14 (m, 1H),
8.01-7.92 (m, 1H),
7.91-7.82 (m, 1H),
7.80 (dd, J=8.4, 8.4 Hz, 2H),
7.72 (dd, J=9.3, 9.3 Hz, 2H),
7.51-7.40 (m, 3H),
7.39-7.16 (m, 5H),
7.12-6.98 (m, 4H),
6.95-6.89 (m, 1H),
3.88-3.70 (m, 3H),
1.52 (d, J=7.2 Hz, 3H);

$^{13}$C NMR (CDCl$_3$): δ

173.4, 158.4, 150.8, 146.6, 138.3, 135.3, 134.6, 134.5, 133.8, 133.7, 131.1, 130.9, 129.1, 128.81, 128.81, 128.6, 127.6, 127.4, 126.7, 126.3, 126.1, 125.8, 125.6, 125.4, 125.1, 125.0, 123.4, 123.3, 119.8, 119.5, 117.1, 115.3, 71.4, 44.9, 27.8, 18.0;

HR MS: calcd for C$_{36}$H$_{27}$NO$_3$Na (M+Na$^+$) 544.1833. found 544.1880.

Analytical data on racemic compound: MP: 189-190° C. (i-PrOH/hexane); IR (KBr); 3055, 1728, 1666, 1427, 1157, 787 cm$^{-1}$.

(No. 59)

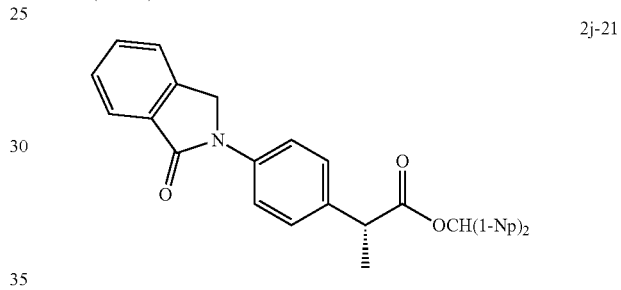

2j-21

(R)-Indoprofen di(1-naphthyl)methyl ester ((R)-2j-21) [90% ee]:

HPLC (CHIRALPAK IC, i-PrOH/hexane=1/1, flow rate=1.0 mL/min):

$t_R$=13.7 min (95.2%), $t_R$=16.8 min (4.8%);

$^1$H NMR (CDCl$_3$): δ

8.37 (s, 1H),
8.07-7.97 (m, 1H),
7.96-7.84 (m, 2H),
7.80 (d, J=8.1 Hz, 2H),
7.78-7.69 (m, 4H),
7.62-7.43 (m, 5H),
7.38 (dd, J=7.2, 7.2 Hz, 1H),
7.34-7.16 (m, 6H),
7.07 (d, J=8.4 Hz, 1H),
4.76 (s, 2H),
3.85 (q, J=7.2 Hz, 1H),
1.53 (d, J=7.2 Hz, 3H);

$^{13}$C NMR (CDCl$_3$): δ

173.4, 167.4, 140.0, 138.5, 135.9, 134.7, 134.5, 133.8, 133.7, 133.1, 132.04, 132.04, 131.2, 130.8, 129.1, 128.83, 128.78, 128.6, 128.43, 128.43, 128.35, 126.7, 126.4, 126.2, 125.8, 125.6, 125.4, 125.2, 125.1, 124.1, 123.4, 123.3, 122.6, 119.5, 71.2, 50.6, 45.1, 18.1;

HR MS: calcd for C$_{38}$H$_{29}$NO$_3$Na (M+Na$^+$) 570.2040. found 570.2018.

Analytical data on racemic compound: MP: 193-194° C. (i-PrOH/hexane); IR (KBr): 3047, 1728, 1697, 1458, 1157, 787 cm$^{-1}$.

(No. 60)

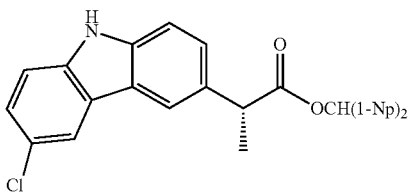

2j-22

(R)-Carprofen di(1-naphthyl)methyl ester ((R)-2j-22) [91% ee]:
HPLC (CHIRALPAK AD-H, i-PrOH/hexane=1/4, flow rate=1.0 mL/min):
$t_R$=9.6 min (95.6%), $t_R$=12.9 min (4.4%);
$^1$H NMR (DMSO-d$_6$): δ
11.4 (s, 1H),
8.28 (s, 1H),
8.23 (s, 1H),
8.10 (d, J=7.5 Hz, 1H),
8.07-7.94 (m, 2H),
7.93 (d, J=8.5 Hz, 1H),
7.89 (d, J=8.5 Hz, 1H),
7.81 (d, J=7.0 Hz, 1H),
7.69 (d, J=8.5 Hz, 1H),
7.67-7.25 (m, 7H),
7.24-7.00 (m, 3H),
6.87 (d, J=7.5 Hz, 1H),
4.22-4.09 (m, 1H),
1.53 (d, J=7.5 Hz, 3H);
$^{13}$C NMR (DMSO-d$_6$): δ
173.4, 140.8, 138.6, 138.5, 134.5, 134.3, 133.6, 133.4, 130.7, 130.3, 129.2, 129.1, 128.9, 128.8, 127.2, 126.7, 126.2, 126.0, 125.9, 125.5, 125.4, 125.1, 125.0, 123.7, 123.1, 123.0, 122.98, 122.95, 121.0, 120.9, 119.9, 118.9, 112.6, 110.3, 70.6, 45.2, 18.7;
Analytical data on racemic compound: MP: 250-251° C. (EtOAc/hexane); IR (KBr): 3356, 3062, 1705, 1466, 1173, 787 cm$^{-1}$.

(No. 61)

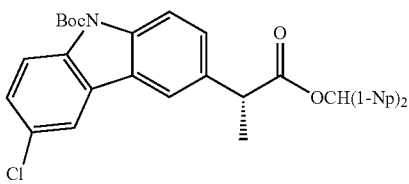

2j-23

(R)—N-Boc-Carprofen di(1-naphthyl)methyl ester ((R)-2j-23) [87% ee]:
HPLC (CHIRALPAK AD-H, i-PrOH/hexane=1/9, flow rate=0.5 mL/min):
$t_R$=14.4 min (93.6%), $t_R$=16.9 min (6.4%);
$^1$H NMR (CDCl$_3$): δ
8.41-8.34 (m, 1H),
8.27 (d, J=8.5 Hz, 1H),
8.13 (s, 1H),
8.00 (d, J=6.5 Hz, 1H),
7.88 (s, 1H),
7.84 (d, J=7.5 Hz, 1H),
7.80-7.64 (m, 5H),
7.46-7.37 (m, 3H),
7.28-7.09 (m, 5H),
7.08-6.99 (m, 2H),
4.06-3.95 (m, 1H),
1.62 (dd, J=7.5, 2.5 Hz, 3H),
1.56 (s, 9H);
$^{13}$C NMR (CDCl$_3$): δ
173.3, 150.5, 139.8, 138.9, 137.2, 134.7, 134.4, 133.8, 133.6, 131.2, 130.8, 129.1, 128.8, 128.7, 128.6, 128.5, 126.9, 126.8, 126.6, 126.22, 126.18, 125.8, 125.5, 125.4, 125.1, 124.9, 123.8, 123.4, 123.3, 123.1, 119.7, 119.2, 117.3, 115.8, 84.2, 71.4, 46.2, 28.1, 18.4;
HR MS: calcd for C$_{41}$H$_{34}$O$_4$NClNa (M+Na$^+$) 662.2069. found 662.2052.
Analytical data on racemic compound: IR (neat): 2978, 1728, 1466, 1157, 764, 741 cm$^{-1}$.

(No. 62)

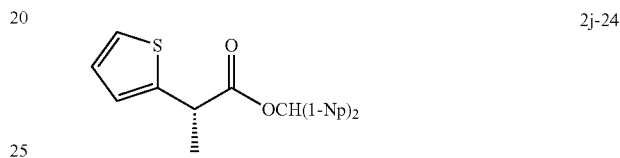

2j-24

Di(1-naphthyl)methyl(R)-2-(2-thienyl)propanoate ((R)-2j-24) [91% ee]:
HPLC (CHIRALPAK AD-H, i-PrOH/hexane=1/9, flow rate=0.5 mL/min):
$t_R$=14.9 min (4.4%), $t_R$=17.5 min (95.6%);
$^1$H NMR (CDCl$_3$): δ
8.38 (s, 1H),
8.03-7.95 (m, 1H),
7.92-7.74 (m, 5H),
7.53-7.38 (m, 3H),
7.37-7.11 (m, 6H),
6.93-6.87 (m, 2H),
4.13 (q, J=7.2 Hz, 1H),
1.59 (d, J=7.2 Hz, 3H);
$^{13}$C NMR (CDCl$_3$): δ
172.5, 142.3, 134.6, 134.4, 133.8, 133.7, 131.1, 130.9, 129.1, 128.9, 128.8, 128.7, 126.7, 126.6, 126.5, 126.0, 125.8, 125.7, 125.4, 125.19, 125.19, 125.1, 124.4, 123.4, 123.3, 71.5, 41.0, 19.2;
HR MS: calcd for C$_{28}$H$_{22}$O$_2$SNa (M+Na$^+$) 445.1233. found 445.1222.
Analytical data on racemic compound: MP: 139-140° C. (EtOAc/hexane); IR (KBr): 3055, 1736, 1450, 1173, 787, 702 cm$^{-1}$.

(No. 63)

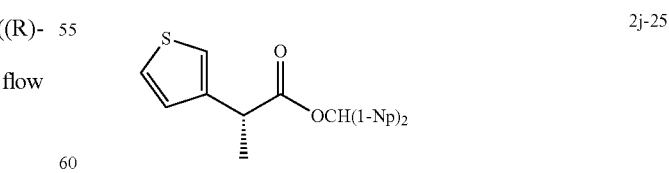

2j-25

Di(1-naphthyl)methyl(R)-2-(3-thienyl)propanoate ((R)-2j-25) [91% ee]:
HPLC (CHIRALPAK AD-H, i-PrOH/hexane=1/9, flow rate=0.5 mL/min):
$t_R$=17.0 min (4.4%), $t_R$=20.1 min (95.6%);
$^1$H NMR (CDCl$_3$): δ

8.36 (s, 1H),
7.98 (d, J=8.5 Hz, 1H),
7.89 (d, J=7.5 Hz, 1H),
7.85 (d, J=8.5 Hz, 1H),
7.82 (d, J=8.5 Hz, 1H),
7.78 (d, J=7.5 Hz, 1H),
7.77 (d, J=7.0 Hz, 1H),
7.53-7.40 (m, 3H),
7.38-7.15 (m, 5H),
7.12-7.05 (m, 2H),
6.98 (d, J=5.0 Hz, 1H),
3.97 (q, J=7.5 Hz, 1H),
1.53 (d, J=7.5 Hz, 3H);
$^{13}$C NMR (CDCl$_3$): δ
173.1, 140.1, 134.8, 134.6, 133.8, 133.7, 131.2, 131.0, 129.1, 128.84, 128.84, 128.7, 127.2, 126.7, 126.4, 126.1, 125.9, 125.7, 125.6, 125.4, 125.2, 125.1, 123.4, 123.3, 121.6, 71.2, 41.2, 17.9;
HR MS: calcd for C$_{28}$H$_{22}$O$_2$SNa (M+Na$^+$) 445.1233. found 445.1214.
Analytical data on racemic compound: MP: 178-179° C. (i-PrOH/hexane); IR (KBr): 3055, 1728, 1450, 1180, 779 cm$^{-1}$.

(No. 64)

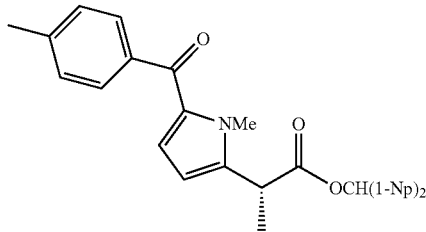

2j-26

Di(1-naphthyl)methyl(R)-2-(2-(1-methyl-5-(4-methyl-benzoyl)pyrrolyl))propanoate ((R)-2j-26) [97% ee]:
HPLC (CHIRALPAK AD-H, i-PrOH/hexane=1/9, flow rate=1.0 mL/min):
$t_R$=28.0 min (98.6%), $t_R$=34.8 min (1.4%);
$^1$H NMR (CDCl$_3$): δ
8.41 (s, 1H),
7.95 (d, J=8.5 Hz, 1H),
7.92-7.76 (m, 5H),
7.71 (d, J=7.5 Hz, 2H),
7.52-7.18 (m, 9H),
7.11 (d, J=7.5 Hz, 1H),
6.66 (d, J=3.5 Hz, 1H),
6.10 (d, J=3.5 Hz, 1H),
3.97 (q, J=7.0 Hz, 1H),
3.75 (s, 3H),
2.42 (s, 3H),
1.60 (d, J=7.0 Hz, 3H);
$^{13}$C NMR (CDCl$_3$): δ
185.8, 171.6, 141.9, 140.1, 137.4, 134.4, 134.3, 133.81, 133.76, 131.2, 131.0, 130.9, 129.41, 129.41, 129.21, 129.15, 128.9, 128.8, 128.67, 128.67, 126.7, 126.6, 125.9, 125.83, 125.83, 125.7, 125.2, 125.1, 123.24, 123.19, 122.3, 107.4, 71.8, 37.7, 33.0, 21.5, 16.3;
HR MS: calcd for C$_{37}$H$_{31}$NO$_3$Na (M+Na$^+$) 560.2196. found 560.2191.
Analytical data on racemic compound: IR (neat): 2985, 1736, 1620, 1458, 1250, 1165, 787, 756 cm$^{-1}$.

(No. 65)

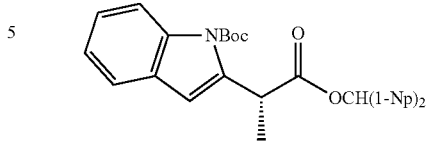

2j-27

Di(1-naphthyl)methyl(R)-2-(2-(1-tert-butyloxycarbonyl)indolyl)propanoate ((R)-2j-27) [87% ee]:
HPLC (CHIRALPAK AD-H, i-PrOH/hexane=1/50, flow rate=0.6 mL/min):
$t_R$=27.6 min (6.6%), $t_R$=33.0 min (93.4%);
$^1$H NMR (CDCl$_3$): δ
8.41 (s, 1H),
8.02 (d, J=8.5 Hz, 1H),
7.97 (d, J=10.0 Hz, 1H),
7.96 (d, J=7.5 Hz, 1H),
7.83 (d, J=7.5 Hz, 1H),
7.81 (d, J=8.5 Hz, 1H),
7.77 (d, J=9.5 Hz, 1H),
7.75 (d, J=8.5 Hz, 1H),
7.46-7.14 (m, 11H),
6.50 (s, 1H),
4.69 (q, J=7.0 Hz, 1H),
1.63 (d, J=7.0 Hz, 3H),
1.42 (s, 9H);
$^{13}$C NMR (CDCl$_3$): δ
172.8, 150.5, 139.6, 136.3, 135.1, 134.6, 133.8, 133.7, 131.2, 131.1, 128.92, 128.88, 128.8, 128.7, 128.6, 126.5, 126.4, 126.3, 126.2, 125.7, 125.6, 125.2, 125.1, 123.83, 123.76, 123.6, 122.6, 120.3, 120.3, 115.7, 108.2, 84.1, 71.6, 40.3, 27.9, 16.9;
HR MS: calcd for C$_{37}$H$_{33}$NO$_4$Na (M+Na$^+$) 578.2302. found 578.2286.
Analytical data on racemic compound: IR (neat): 2978, 1736, 1705, 1458, 1157, 779, 756 cm$^{-1}$.

(No. 66)

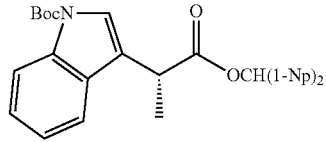

2j-28

Di(1-naphthyl)methyl(R)-2-(3-(1-tert-butyloxycarbonyl)indolyl)propanoate ((R)-2j-28) [99% ee]:
HPLC (CHIRALPAK AD-H, i-PrOH/hexane=1/9, flow rate=0.5 mL/min):
$t_R$=11.3 min (0.3%), $t_R$=21.7 min (99.7%);
$^1$H NMR (CDCl$_3$): δ
8.37 (s, 1H),
8.13 (d, J=8.1 Hz, 1H),
7.92 (d, J=8.4 Hz, 1H),
7.88 (d, J=7.8 Hz, 1H),
7.82 (d, J=8.1 Hz, 1H),
7.81 (d, J=8.1 Hz, 1H),
7.54 (d, J=8.4 Hz, 1H),
7.51-7.34 (m, 5H),
7.32-7.02 (m, 7H),
4.07 (q, J=7.2 Hz, 1H),
1.66-1.60 (m, 12H);
$^{13}$C NMR (CDCl$_3$): δ

173.3, 149.6, 134.6, 134.4, 133.8, 133.7, 131.1, 130.9, 129.0, 128.9, 128.8, 128.6, 126.6, 126.4, 126.0, 125.8, 125.71, 125.71, 125.1, 125.0, 124.45, 124.45, 123.43, 123.38, 123.17, 123.17, 122.4, 119.47, 119.41, 115.1, 83.6, 71.6, 37.1, 28.2, 17.0;

HR MS: calcd for $C_{37}H_{33}NO_4Na$ (M+Na$^+$) 578.2302. found 578.2285.

Analytical data on racemic compound: IR (neat): 2978, 1736, 1728, 1458, 1157, 787, 756 cm$^{-1}$.

The invention claimed is:

1. A method for manufacturing an optically active carboxylic acid ester, the method comprising:

reacting a racemic carboxylic acid and an alcohol represented by formula (a) below or a phenol derivative represented by formula (b) below under the presence of an acid anhydride and an asymmetric catalyst in a polar solvent with a dipole moment of 3.72 or higher, wherein formula (a) has the structure

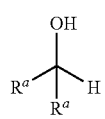

(a)

where $R^a$ represents a phenyl group, naphthyl group, anthryl group, or phenanthryl group, which may have a substituent group, and formula (b) has the structure

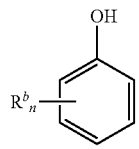

(b)

where $R^b$ represents a phenyl group, naphthyl group, anthryl group, or phenanthryl group, which may have a substituent group, n represents an integer of 1 to 5, and in the case that a plurality of $R^b$ is present, they may be the same or different.

2. The method for manufacturing an optically active carboxylic acid ester according to claim 1, wherein the asymmetric catalyst is represented by formulas (c) to (f) below:

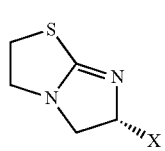

(c)

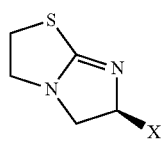

(d)

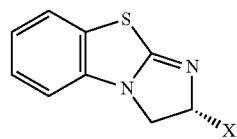

(e)

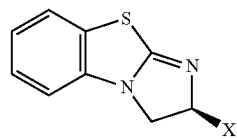

(f)

where X represents any of the following substituent groups,

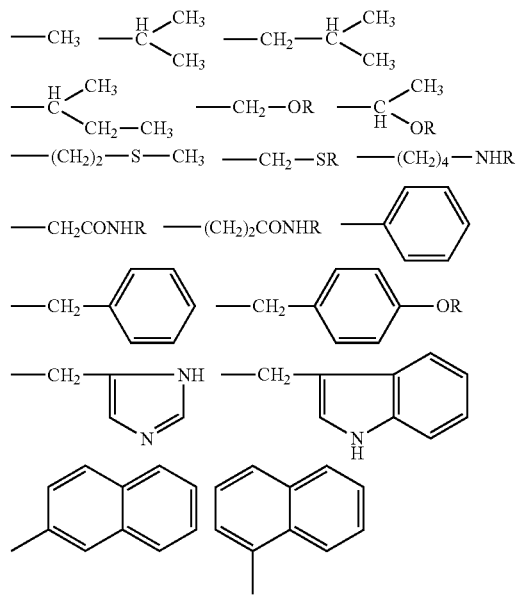

and R represents a protecting group.

3. The method for manufacturing an optically active carboxylic acid ester according to claim 1, wherein the racemic carboxylic acid is represented by formula (g) below:

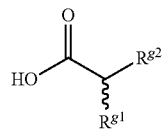

(g)

wherein $R^{g1}$ and $R^{g2}$ represent organic groups which differ from each other.

4. The method for manufacturing an optically active carboxylic acid ester according to claim 3, wherein either one of $R^{g1}$ and $R^{g2}$ in the formula (g) is an organic group that binds to an asymmetric carbon via a carbon atom having a multiple bond, and the other one is an organic group that binds to an asymmetric carbon via a carbon atom not having a multiple bond.

5. The method for manufacturing an optically active carboxylic acid ester according to of claim 4, wherein the organic group binding with an asymmetric carbon via a carbon atom having a multiple bond is an aryl group or heteroaryl group; and the organic group binding with an asymmetric carbon via a carbon atom not having a multiple bond is an alkyl group.

6. The method for manufacturing an optically active carboxylic acid ester according to claim 3, wherein, in the formula (g), one of either of $R^{g1}$ and $R^{g2}$ is an aryl group or heteroaryl group, and the other is an alkyl group.

7. The method for manufacturing an optically active carboxylic acid ester according to claim 1, wherein the racemic carboxylic acid is ibuprofen, ketoprofen, fenoprofen, flurbiprofen, naproxen, loxoprofen, pranoprofen, indoprofen, carprofen, or N-Boc-carprofen.

8. The method for manufacturing an optically active carboxylic acid ester according to claim 1, wherein the polar solvent is at least one selected from the group consisting of N-methylpyrrolidone, N,N-dimethylformamide, N,N-dimethylacetamide, 1,3-dimethyl-2-imidazolidine and dimethylsulfoxide.

9. The method for manufacturing an optically active carboxylic acid ester according to claim 1, wherein the polar solvent is at least one selected from the group consisting of N,N-dimethylformamide and N,N-dimethylacetamide.

10. The method for manufacturing an optically active carboxylic acid ester according to claim 1, wherein the alcohol represented by formula (a) is di(1-naphthyl)methanol.

11. The method for manufacturing an optically active carboxylic acid ester according to claim 1, wherein the acid anhydride is at least one selected from the group consisting of benzoic anhydrides which may be bonded to an electron-donating group, and multisubstituted carboxylic acid anhydrides where the α-position is a quaternary carbon.

12. The method for manufacturing an optically active carboxylic acid ester according to claim 1, wherein the acid anhydride is at least one selected from the group consisting of benzoic anhydride, a 1 to 3 substituted benzoic acid anhydride with alkyl groups or alkoxy groups of 1 to 3 carbons bonded thereto, pivalic acid anhydride, 2-methyl-2-phenylpropionic acid anhydride, and 2,2-diphenylpropionic acid anhydride.

13. The method for manufacturing an optically active carboxylic acid ester according to claim 1, wherein the acid anhydride is pivalic acid anhydride.

14. The method for manufacturing an optically active carboxylic acid ester according to claim 1, wherein the asymmetric catalyst is at least one selected from the group consisting of tetramisole and benzotetramisole.

15. The method for manufacturing an optically active carboxylic acid ester according to claim 1, wherein the reaction is carried out under the presence of a base.

16. The method for manufacturing an optically active carboxylic acid ester according to claim 15, wherein the base is at least one selected from the group consisting of trimethylamine, triethylamine, and diisopropylethylamine.

17. The method for manufacturing an optically active carboxylic acid ester according to claim 1, wherein the racemic carboxylic acid is ibuprofen, the alcohol represented by the formula (a) is di(1-naphthyl)methanol, the acid anhydride is pivalic acid anhydride, and the asymmetric catalyst is benzotetramisole, and the polar solvent is N,N-dimethylformamide.

18. The method for manufacturing an optically active carboxylic acid ester according to claim 1, wherein the reaction selectively esterifies one of the enantiomers of the racemic carboxylic acid, while racemizing the other enantiomer.

19. The method for manufacturing an optically active carboxylic acid ester according to claim 1, wherein the alcohol or phenol derivative is added in an amount of 1.0 to 1.5 equivalents relative to the racemic carboxylic acid.

* * * * *